(12) United States Patent
Balss et al.

(10) Patent No.: US 7,478,008 B2
(45) Date of Patent: Jan. 13, 2009

(54) SYSTEM AND METHOD FOR THE NON-DESTRUCTIVE ASSESSMENT OF THE QUANTITATIVE SPATIAL DISTRIBUTION OF COMPONENTS OF A MEDICAL DEVICE

(75) Inventors: Karin Maria Balss, King of Prussia, PA (US); Gerard Llanos, Stewartsville, NJ (US); Cynthia Anne Maryanoff, New Hope, PA (US); George Papandreou, Kendall Park, NJ (US); Vladimir Veselov, Newtown, PA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 11/780,342

(22) Filed: Jul. 19, 2007

(65) Prior Publication Data

US 2008/0228428 A1    Sep. 18, 2008

Related U.S. Application Data

(60) Provisional application No. 60/895,242, filed on Mar. 16, 2007.

(51) Int. Cl.
*G06F 15/00* (2006.01)
(52) U.S. Cl. ..................................... 702/137
(58) Field of Classification Search .................. 702/32, 702/137, 152, 180, 189, 190, 191; 356/326, 356/432, 630, 317, 318; 600/407, 473, 476; 250/339.05, 339.07, 339.11
See application file for complete search history.

(56) References Cited

U.S. PATENT DOCUMENTS

| | | | | |
|---|---|---|---|---|
| 4,654,593 | A * | 3/1987 | Ackerman | 324/307 |
| 6,734,962 | B2 * | 5/2004 | Treado et al. | 356/301 |
| 6,957,152 | B1 | 10/2005 | Esbeck | |
| 7,048,962 | B2 | 5/2006 | Shekalim et al. | |
| 7,263,463 | B2 * | 8/2007 | Yamazaki | 702/182 |
| 2003/0087024 | A1 | 5/2003 | Flanagan | |
| 2006/0282223 | A1 * | 12/2006 | Lewis et al. | 702/19 |

FOREIGN PATENT DOCUMENTS

WO    WO 2004/038602 A1    5/2004

* cited by examiner

*Primary Examiner*—Bryan Bui
(74) *Attorney, Agent, or Firm*—William A. Schoneman

(57) ABSTRACT

A method and system for the non-destructive analysis of medical devices uses a confocal Raman microscope and other non-destructive analytical tools to assess the spatial distribution of components of an object such as the distribution of an active pharmaceutical ingredient (API) within a polymer matrix. In a preferred embodiment, confocal Raman spectroscopy was used to differentiate each component found in the sirolimus-eluting coronary stent. The unique spectral features identified for each component were then used to develop three separate calibration curves to describe the solid phase distribution found on drug-polymer coated stents. The calibration curves were obtained by analyzing confocal Raman spectral depth profiles from a set of 16 unique formulations of drug-polymer coatings sprayed onto stents and planar substrates.

40 Claims, 27 Drawing Sheets

Chemical Formula: $C_{51}H_{79}NO_{13}$

Molecular Weight: 914.17

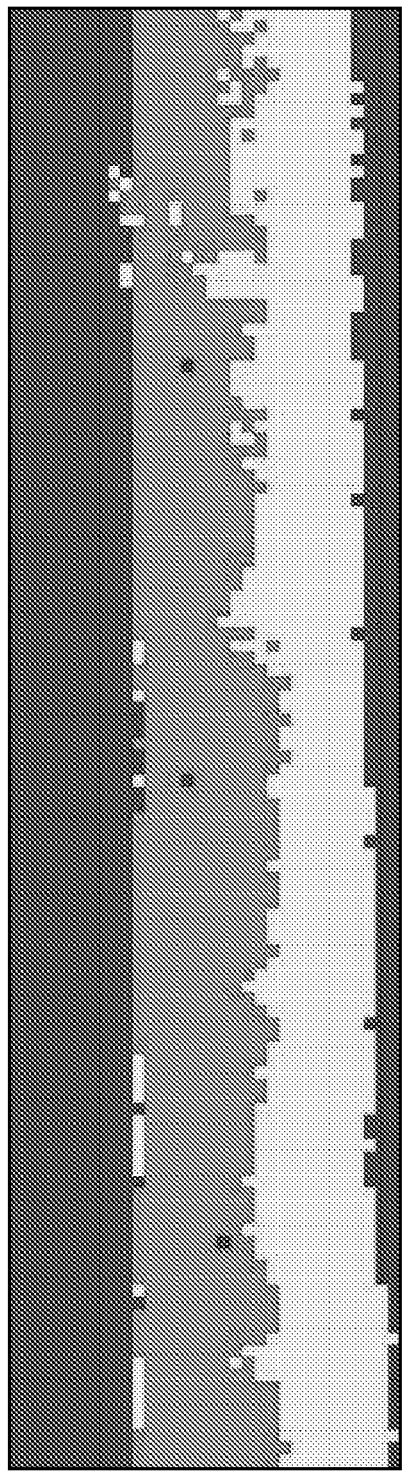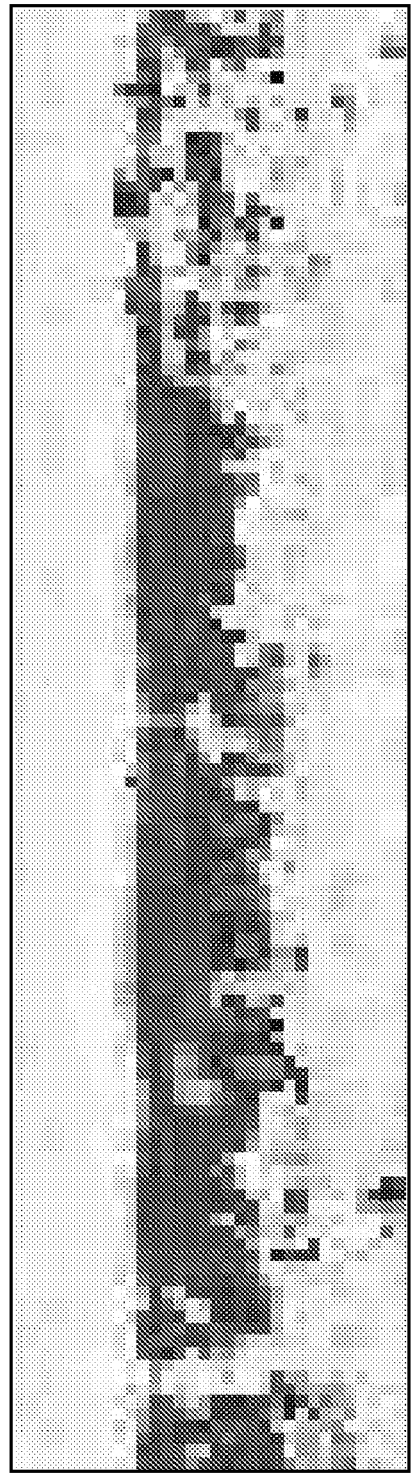
FIG. 24A
FIG. 24B

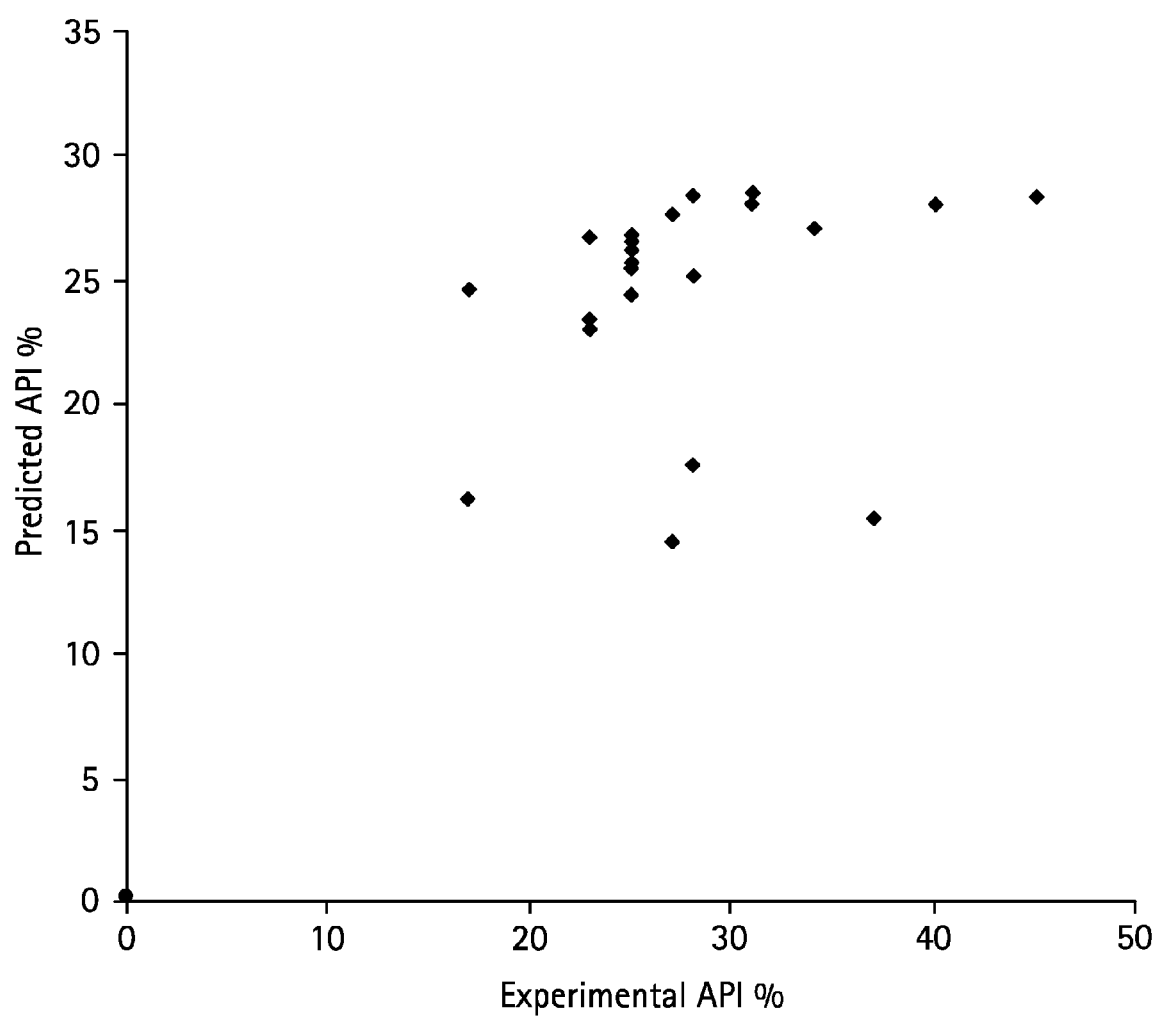

SYSTEM AND METHOD FOR THE NON-DESTRUCTIVE ASSESSMENT OF THE QUANTITATIVE SPATIAL DISTRIBUTION OF COMPONENTS OF A MEDICAL DEVICE

CROSS REFERENCE TO RELATED APPLICATION

This application claims the benefit of U.S. Provisional Application No. 60/895,242 filed Mar. 16, 2007.

FIELD OF THE INVENTION

The present invention relates to a system and method for the non-destructive, chemically specific, profiling and assessment of the spatial distribution of the therapeutic agents and other components of a substance applied to an object such as a medical device. More particularly, the invention relates to a system and method to determine that therapeutic agent or agents have been accurately applied to a medical device such as a drug-eluting stent so as to confirm the elution profile of the stent over time thereby providing an empirical link between the macroscopic properties of the device with the microscopic distribution of components within the device.

BACKGROUND OF THE INVENTION

Many individuals suffer from circulatory disease caused by a progressive blockage of the blood vessels that profuse the heart and other major organs with nutrients. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting.

Restenosis after percutaneous transluminal coronary angioplasty is a gradual process initiated by vascular injury. Multiple processes, including thrombosis, inflammation, growth factor and cytokine release, cell proliferation, cell migration and extracellular matrix synthesis each contribute to the restenotic process.

Stents have proven useful in significantly reducing restenosis. Typically, stents are balloon-expandable slotted metal tubes, which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing the incidence of restenosis at six months.

Additionally, the coating of stents appears to have the added benefit of producing a reduction in sub-acute thrombosis after stent implantation. Stents coated with various pharmacological agents to prevent restenosis have been available for several years. One such agent is sirolimus (also referred to as rapamycin). Sirolimus is a macroyclic triene antibiotic produced by streptomyces hygroscopicus as disclosed in U.S. Pat. No. 3,929,992. It has been found that sirolimus among other things inhibits the proliferation of vascular smooth muscle cells in vivo. Accordingly, sirolimus may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Sirolimus functions to inhibit smooth muscle cell proliferation and does not interfere with the re-endothelialization of the vessel walls.

Sirolimus may be incorporated into or affixed to the stent in a number of ways. In the exemplary embodiment, the sirolimus is directly incorporated into a polymeric matrix and sprayed onto the surface of the stent. The sirolimus elutes from the polymeric matrix over time and enters the surrounding tissue. The sirolimus preferably remains on the stent for at least three days up to approximately six months, and more preferably between seven and thirty days.

Any number of non-erodible polymers may be utilized in conjunction with the sirolimus. The sirolimus is incorporated into this polymeric base layer. Essentially, the sirolimus elutes from the matrix by diffusion through the polymer molecules. Polymers are permeable, thereby allowing solids, liquids and gases to escape therefrom. The total thickness of the polymeric matrix is in the range from about 1 micron to about 20 microns or greater.

Other therapeutic agents may be similarly applied to stents in order to reduce restenosis. One important consideration regarding the process for applying the coatings is the spatial distribution of the therapeutic agent in all three coordinate directions. Accordingly there exists a need for determining the spatial distribution of the therapeutic agent across around and into the coating matrix applied to a medical device such as a stent. It would be desirable to have a spatial distribution of the therapeutic agent rather than merely a bulk analysis of the stent.

Such drug-eluting stents (DES) effectively treat restenosis, the re-occlusion of blood vessels that occurs after percutaneous balloon angioplasty or stenting. The devices are typically described by the amount of drug they contain (drug dose) and how the drug is released temporally in vivo (elution profile) because the clinical effectiveness of DES is dependent on both of these performance indicators. Factors influencing these performance parameters include the stent platform design, drug and polymer formulation, and drug release strategy. The physical stent platform design impacts the local delivery of the drug in vitro. Also, there is a correlation between the drug dose and elution profile to the spatial location of drug within the polymer matrix. Strategies for modifying the drug elution profile rely on changing the drug loading relative to polymer, changing the physical and mechanical properties of the polymer matrix, or creating reservoir or degradable systems. Prior analysis was based on surface characterizations of the solid-state distribution of drug which neglected to describe the distribution within the three-dimensional polymer matrix.

One currently-marketed DES is the CYPHER® Sirolimus-eluting Coronary Stent. The CYPHER® Stent product has a coating that is an immiscible blend of poly (ethylene-co-vinyl acetate) [PEVA], poly (n-butyl methacrylate) [PBMA] and sirolimus. The coating is applied on a poly (o-chloro-p-xylylene) [parylene-C] treated stainless steel stent. The coating contains 140 µg of sirolimus per $cm^2$ of stent surface area and elutes during 30 days in vivo. Currently, this drug-polymer coating is described in the literature solely on the basis of its manufacturing method. The manufacture of the CYPHER® Stent product consists of first applying a basecoat solution containing PEVA, PBMA, and sirolimus. An inactive topcoat solution and toluene overspray follows the basecoat solution application. Early in the history of CYPHER® Stent product it was assumed that the manufacturing sequence of solutions dictated the final distribution of drug and polymer. However, this assumption proved invalid because the influence of mixing and drying that occurs during manufacture was not considered. The final spatial distribution of sirolimus and polymers has not been reported. It would be desirable to understand the drug's spatial profile within the matrix in order to describe and predict the performance of the CYPHER® Stent product (drug dose and elution profile).

The appropriate strategy for spatially mapping components of drug-polymer coatings should utilize both chemical and physical mapping techniques. Atomic force microscopy (AFM) and scanning electron microscopy (SEM) are both routinely used to characterize the physical attributes of stent coatings. AFM is useful for physical descriptions such as surface topography and identifying component domains. SEM is useful to describe the coating conformity to the stent pre- and post-expansion. Both techniques are coating surface limited and do not adequately represent the three-dimensional system. The techniques also lack the chemical specificity to positively differentiate drug from polymer matrix components. Another surface sensitive technique that provides chemical information is X-ray photoelectron spectroscopy. XPS has been used to characterize surfaces of several drug-polymer stent coatings including confirmation of drug and the determination of possible chemical reactions with the matrix components.

Dynamic time-of-flight mass spectrometry performs destructive depth profiles through drug-polymer coatings for chemically specific information. Spectroscopic methods such as near infrared (NIR), Fourier transform infrared (FTIR), and Raman spectroscopy are nondestructive approaches that provide the chemical specificity needed to distinguish an active pharmaceutical ingredient (API) from the matrix components. Although NIR and FTIR imaging provide chemical selectivity, both suffer from poor spatial resolution and cannot depth profile through coatings. Fluorescence microscopy requires chemical labeling of the drug or a fluorophore inherent to the system. Fluorescence microscopy has been used to describe the uniformity of hyaluronan layers on stainless steel stents. Fluorescence imaging has also used to describe drug delivery in vitro and in vivo.

Previous work by the S. L. Hsu, author of "Raman Spectroscopic Analysis of Drug Delivery Systems," American Pharmaceutical Review 2006, pp 58-64 has provided qualitative depth information about the solid phase distribution of drugs on stents. Raman spectroscopy is established as a reliable quantitative tool. Quantitative CRM has emerged recently and was successful in describing interfaces of adhesives to dentin, drugs in solid dispersions, and polymer blends. Coherent anti-Stokes Raman scattering confocal microscopy was recently utilized to image drug distribution and subsequent release from polymer coatings. The requirements for the ideal method to quantify components present in DES is that it must be non-destructive, chemically specific to both API and matrix components, quantitative, possess depth profiling capabilities, high spatial resolution, and have practical analysis times.

Chemometrics is a field that refers to the analysis of chemical data by statistical methods of analysis. Chemometrics is useful for the analysis of complex mixtures and assessing the performance of a process. Examples of chemometric analyses relevant to the pharmaceutical industry include at-line control, analysis of moisture in tablets via NIR and investigation of polymorphs via Raman spectroscopy. Chemometrics is a tool that can increase the throughput of sample analysis.

It would be desirable to have a system and method for quantifying components present in DES that is non-destructive, chemically specific to both API and matrix components, quantitative, capable of providing depth profiling, having high spatial resolution, and having practical analysis times.

Furthermore, it would be desirable to have a system for the non-destructive analysis of drug-coated medical devices other than drug-eluting stents. Additionally, it is desirable to have a platform that can be used for the non-destructive analysis of products other than medical devices.

Additionally, it would be desirable to have a system that combines the capabilities of confocal Raman microscopy and other non-destructive analysis tools with the statistical methods of chemometrics in order to accomplish the non-destructive analysis of medical devices and other products in an efficient and rigorous manner.

SUMMARY OF THE INVENTION

The present invention is an application of confocal Raman microscopy (CRM) and other non-destructive analytical methods to provide a tool for the analysis of the three-dimensional profile of drug-eluting stents and other medical devices and objects. There are two principle techniques in the CRM instrument that in combination create a nondestructive, chemically specific tool. Placing a pinhole at the detection plane allows the microscope to selectively image depth planes in transparent or semi-transparent coatings. The confocal microscope is combined with a high throughput Raman spectrometer for nondestructive, chemically specific spatial depth mapping.

The aim of the present invention is to provide a system and method for describing the spatial homogeneity of the drug and polymers in the stent coatings or other objects and to quantify each by a nondestructive, chemically specific test method. The present work describes the unique vibrational spectrum for each component found in the CYPHER® Stent product by Raman spectroscopy. CRM was successfully utilized to qualitatively map the microscopic distribution of sirolimus within the polymer coating with superior spatial resolution (1 μm depth) compared to other microscopic methods. The CRM response as a function of drug-polymer formulation to develop a quantitative calibration curve for sirolimus relative to polymer content was monitored. The polymer components were also quantified in separate calibration curves. The feasibility of the CRM method as a quantitative spatial tool has been tested on independent drug-polymer coated stents. The sirolimus content predictions on the independent sample sets are compared to a laboratory assay value for determination of accuracy whereas the individual polymer content predictions are compared to solution concentrations for qualitative comparisons.

In the present system for the non-destructive analysis of the spatial distribution of one or more components of an object, a sample and analysis tracking module is used for collecting and storing information about the object such as the fabrication date of the object, the type of object and the analysis date for analysis of the object. An analysis processing module collects data regarding the distribution of components of the object and a description of how the data was collected. A data processing module analytically processes the data to determine the spatial distribution of the one or more components of the object. A central database that receives and stores data from the analysis processing module and the data processing module as well as the sample and analysis tracking module.

The analysis processing module comprises an analytical instrument for collecting information about the object. Such analytical instrument may be a confocal Raman microscope or some other non-destructive analytical tool such as a confocal fluorescence microscope, a scanning polarized and phase light microscope, an x-ray photoelectron imaging system, a near IR Imaging system and a dynamic static ionization mass spectrometer (dynamic SIMS). The analysis processing module further comprises a positioning device for controlling the position of the object relative to the analytical instrument and may also include a bar code scanner for reading an identifying bar code on the object. These elements of the analysis processing module are controlled by a programmable logic controller for controlling the functions of the analytical instrument, positioning device and bar code scanner and for collecting the analysis data and forwarding it to the data processing module.

The output of the data processing module includes information about the composition of the components of the object, the spatial distribution of components in the object and identification of manufacturing and formulation defects of the object. This information can be presented to the user as either a visual representation or a numeric representation. The data processing module filters data received from the analysis processing module to remove noise such as the noise from cosmic rays or the laser line at the detector of a confocal Raman microscope. The data processing module uses a clustering algorithm such as the K-means clustering algorithm to pre-process the data prior to identification of components and their spatial distributions. Training sets and validation sets for each type of object to be analyzed are retrieved from the central database and are compared to the pre-processed data in order to build a model of the quantitative spatial distribution of the components in the object. Calibration of the model using PCA and linear regression techniques and finally a visualization or numerical representation of the quantitative spatial distribution of components of the object is the output to the user.

BRIEF DESCRIPTION OF THE DRAWINGS

FIG. 24*a* shows an example cluster image after a preprocessed data set was subjected to K-mean cluster analysis.

FIG. 24*b* is a quantitative visual representation of a stent using the present method and system.

FIG. 25 is a plot of predicted API weight % versus experimental API wt %.

DETAILED DESCRIPTION OF THE INVENTION

Figure 1:
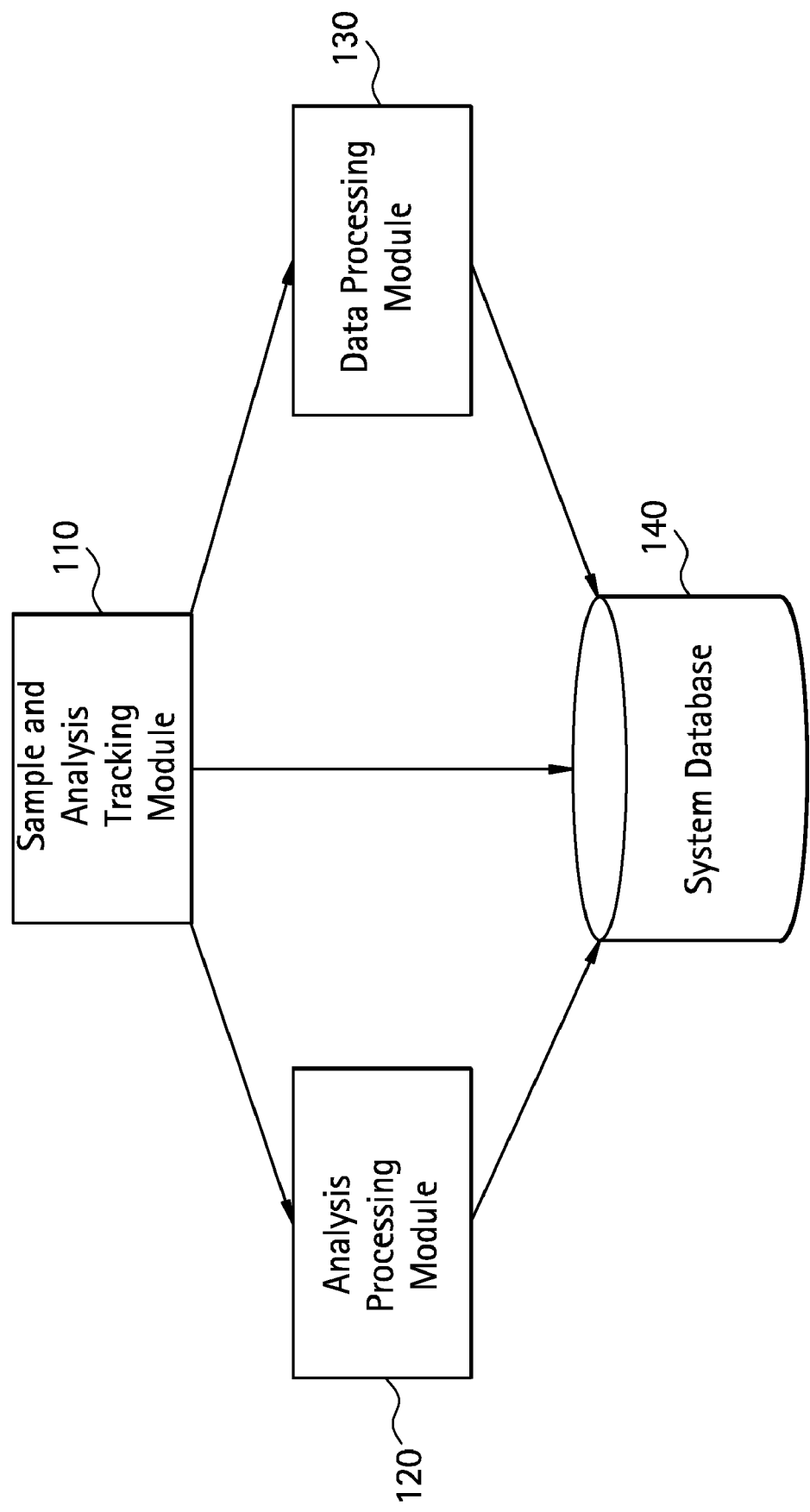
FIG. 1 depicts a schematic of a system in accordance with the present invention.

The schematic diagram of the system of the present invention is set forth FIG. 1. There are three separate modules and a system database. Sample and analysis tracking module 110 enables the user of the system to input data regarding the sample to be analyzed and tracks the progress of the sample through the analysis process. The sample and analysis tracking module 110 will store information about the sample such as a description of the sample (formulation of API and matrix components and process type of sample device), fabrication date, and the analysis date in the system database 140. The analysis processing module 120 comprises an instrument to collect the data and a also retains a description of how the data is collected including the type of instrument, sample positioning, number of observations, and type of data collected. The data processing module 130 processes the data collected from the analysis processing module 120 analytically. The output from the data processing module is then used to guide decision-making regarding metrics such as the quality, performance, or the characteristics of a sample. Some examples of simple outputs would include API content, API distribution, matrix content, matrix distribution, thickness and identification of manufacturing and formulation defects. These outputs can be displayed as a visual or numeric representation. A central system database 140 receives and stores input from the analysis processing module and the data processing module.

Figure 2:
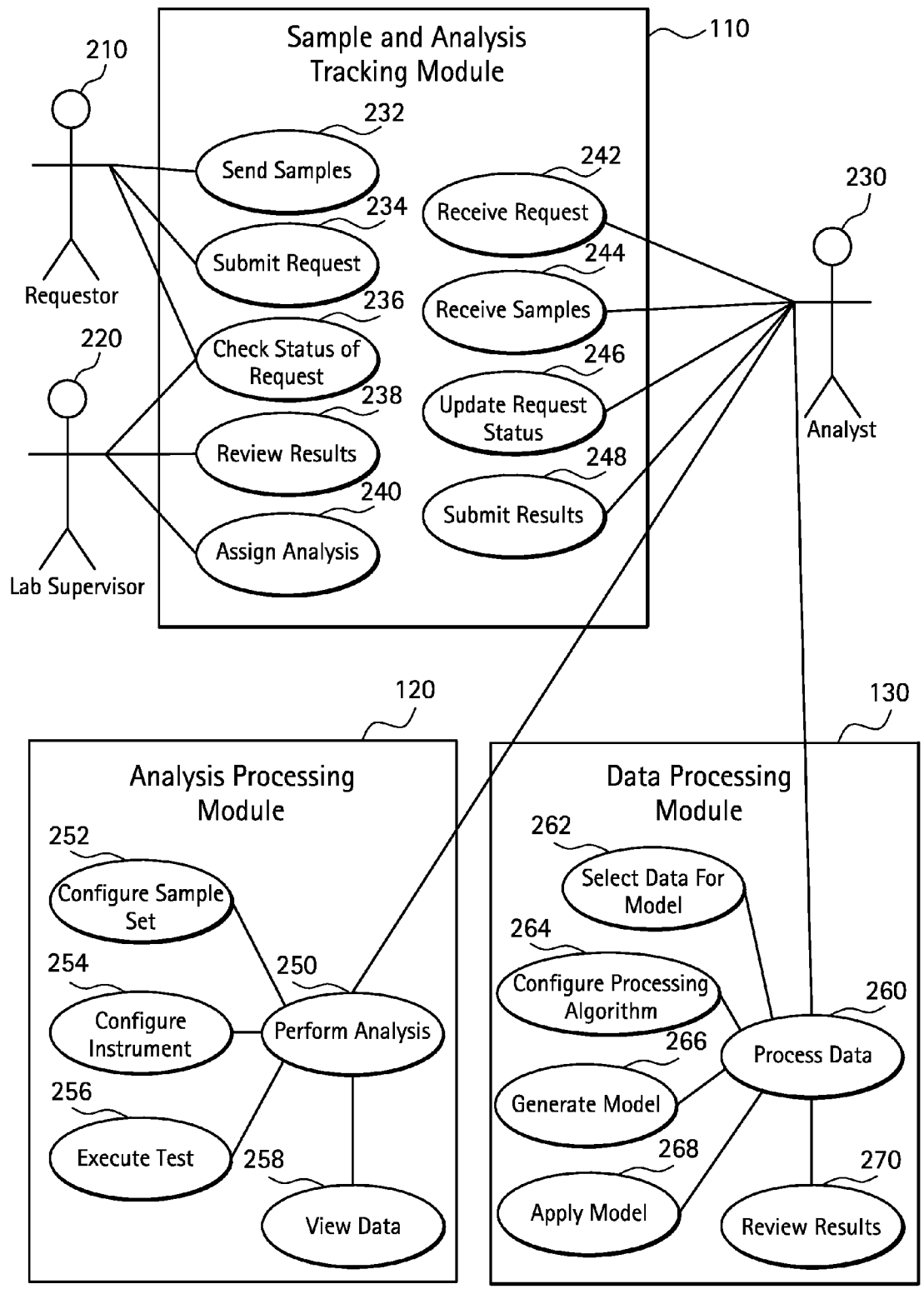
FIG. 2 depicts the flow of actions and data within a system in accordance with the present invention.

FIG. 2 depicts the flow of actions and data within a system in accordance with the present invention. The sample and analysis tracking module 110 can be used by the requester 210 to send samples 232, submit requests 234, check the status of requests 236 and review results 238. A lab supervisor 220 would use the sample and analysis tracking module to check the status of requests 236, review results 238 and assign analysis 240 to a trained analyst. An analyst 230 interacts with the sample and analysis tracking module to receive requests 242, receive samples 244, update request status 246 and submit results 248. The analyst uses the analysis processing module 120 to perform the analysis of the sample 250 which comprises the steps of configuring the sample set 252, configuring the analysis instrument 254, executing the test 256 and viewing data 258. The data processing module 130 is used by the analyst 230 to process data 260 comprising the steps of selecting data for the model 262, configuring the processing algorithm 264, generating the model 266, applying the model 268 and reviewing the results 270.

Figure 3:
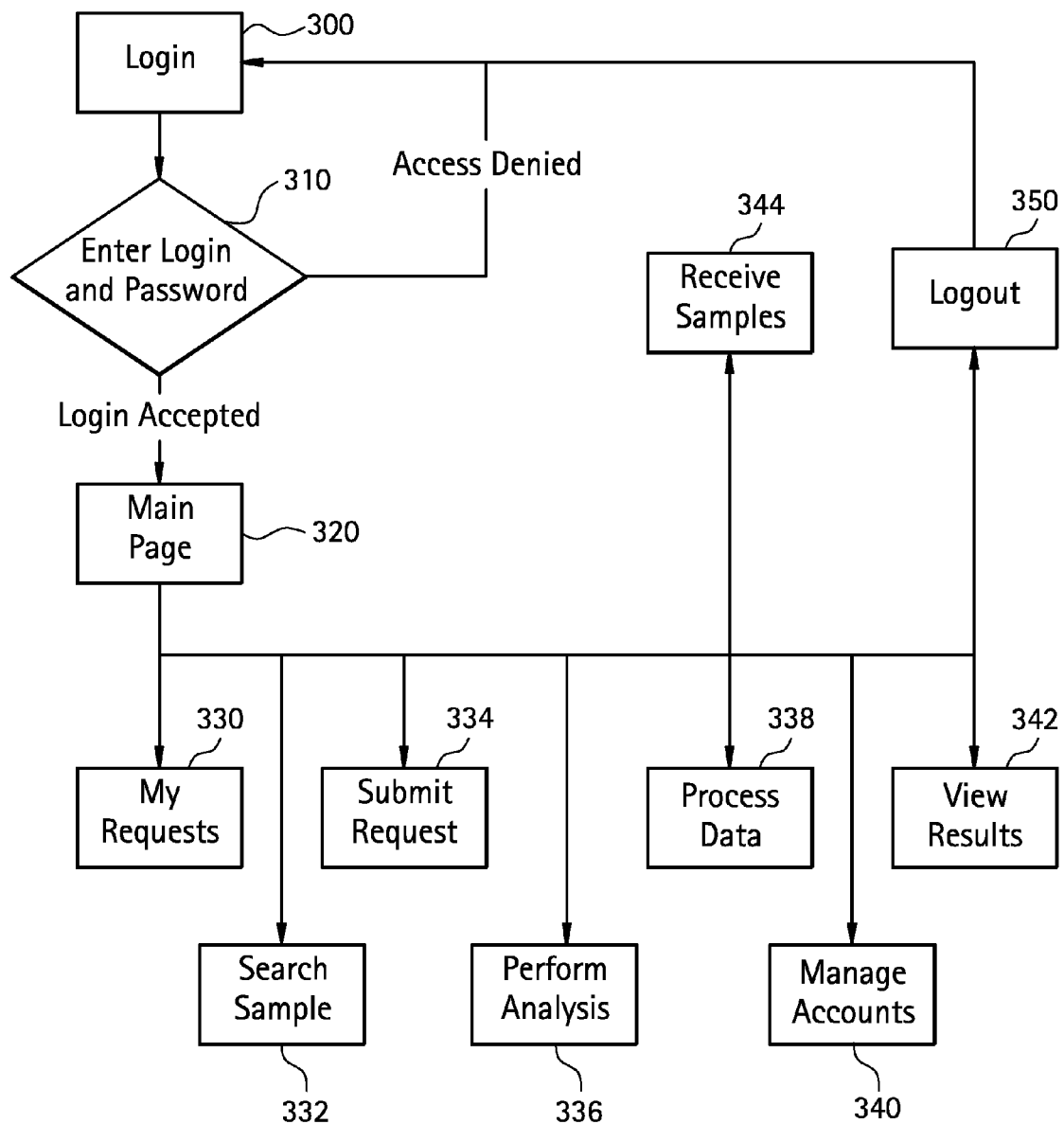
FIG. 3 depicts the process flow within the user interface of the sample analysis and tracking module of a system in accordance with the present invention.

FIG. 3 is a flow diagram depicting the process flow of the user interface within the sample and analysis tracking module 110. The sample analysis and tracking module 110 provides a user interface to the system of the present invention. A user accesses the system by performing a login at step 300. At step 310 the login and password are checked and the user is either permitted access to the main page at step 320 or is denied access and returned to the login screen at step 300. The main page presents seven different choices to the user. The "My Request" function at step 330 provides the user with the ability to view data regarding various analysis requests placed into the system by the user and to input or edit information about the requests. This function is detailed below in the discussion of FIG. 4. The "Search Sample" function at step 332 enables the user to search the database of previously analyzed samples and results. This function detailed below in the discussion of FIG. 5. At step 334 the user can submit a request for analysis to the analysis processing module 120. This function is detailed below in the discussion of FIG. 6. The user can request to perform analysis at step 336 and the analysis processing module 120 will generate data as described below which will result in creation of an analysis data file which can then be processed at step 338 by the data processing module 130. The user may also perform account management functions at step 340 which is detailed below with respect to FIG. 7. The user can view results through the use of the "View Results" function 342 and can input samples through the "Receive Sample" function 344. At step 350 the user can logout from the system when finished with the analysis and processing of samples. The sample and analysis tracking module 110 of the present invention can be implemented in software on any general purpose computer such as a personal computer, workstation or microcomputer. The module may be implemented in any programming language such as JAVA, ColdFusion or .NET. The preferred embodiment of the systems has been implemented in the ColdFusion programming language.

Figure 4:
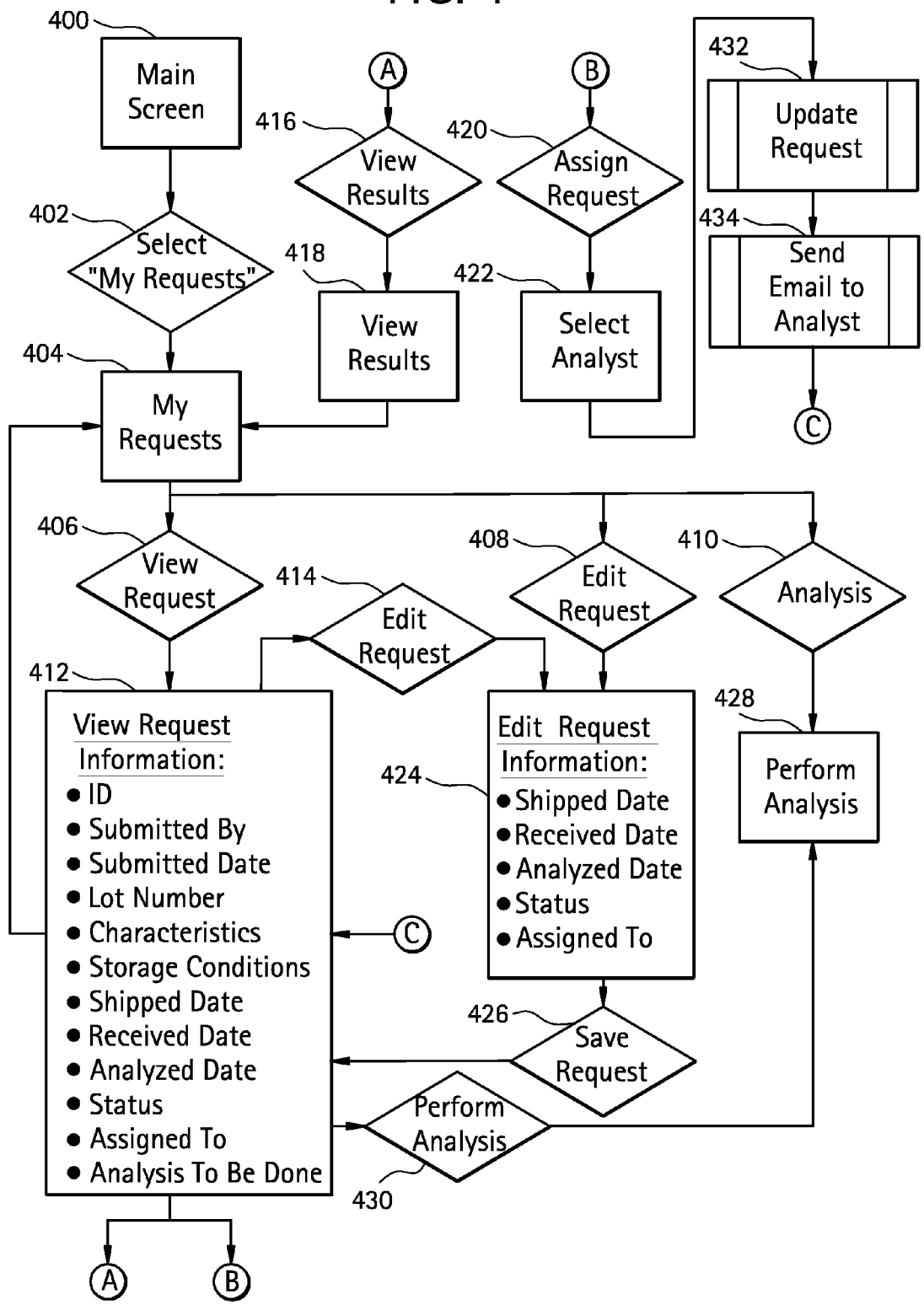
FIG. 4 depicts the process flow within the sample analysis and tracking module of a system in accordance with the present invention when a user selects to review and edit requests for analysis.

FIG. 4 depicts the process flow within the sample analysis and tracking module 110 of when a user selects to review and edit requests for analysis. Main user interface screen 400 displays the selections discussed above. If the user selects "My Requests" at step 402, then the following options are available to the user under the "My Request Menu" displayed at step 404. The user may either select to view requests at step 406, edit requests at step 408 or perform analysis at step 410. If the user selects to review requests then some or all of the following information is displayed at step 412: sample identification, name of submitter, date of submission, lot number, characteristics of the sample, storage conditions for the sample, shipping date, receipt data, analysis date, status, analyst assigned to the sample and a description of the analysis to be done on the sample. After review of the request information the user may either decide to edit request at step 414, view results at step 416, assign the request to an analyst at step 420 or have the analysis performed at step 430. If the edit request function is selected at either step 408 or step 414 then the user is able to edit one or more of the following pieces of information at step 424: the shipping date, the received date, the analysis date, status or the analyst assigned to the sample. The edited request is then saved at step 426 and the edited request is displayed again at step 412. If the user selects the perform analysis function at either step 410 or step 430 then the system performs the analysis at step 428 in accordance with the process flow depicted in FIG. 9. If the user selects the view results function at step 16 then results are displayed in accordance with the process flow depicted in FIG. 15 and the user is returned to the "My request" screen upon completing review. If the user selects the assign request function at step 420 then an analyst 230 is selected to perform the analysis at step 422, the request is updated at 432 to reflect the identity of the assigned analyst and an e-mail message is sent to the assigned analyst 230 at step 434 to notify the analysts of the assignment.

Figure 5:
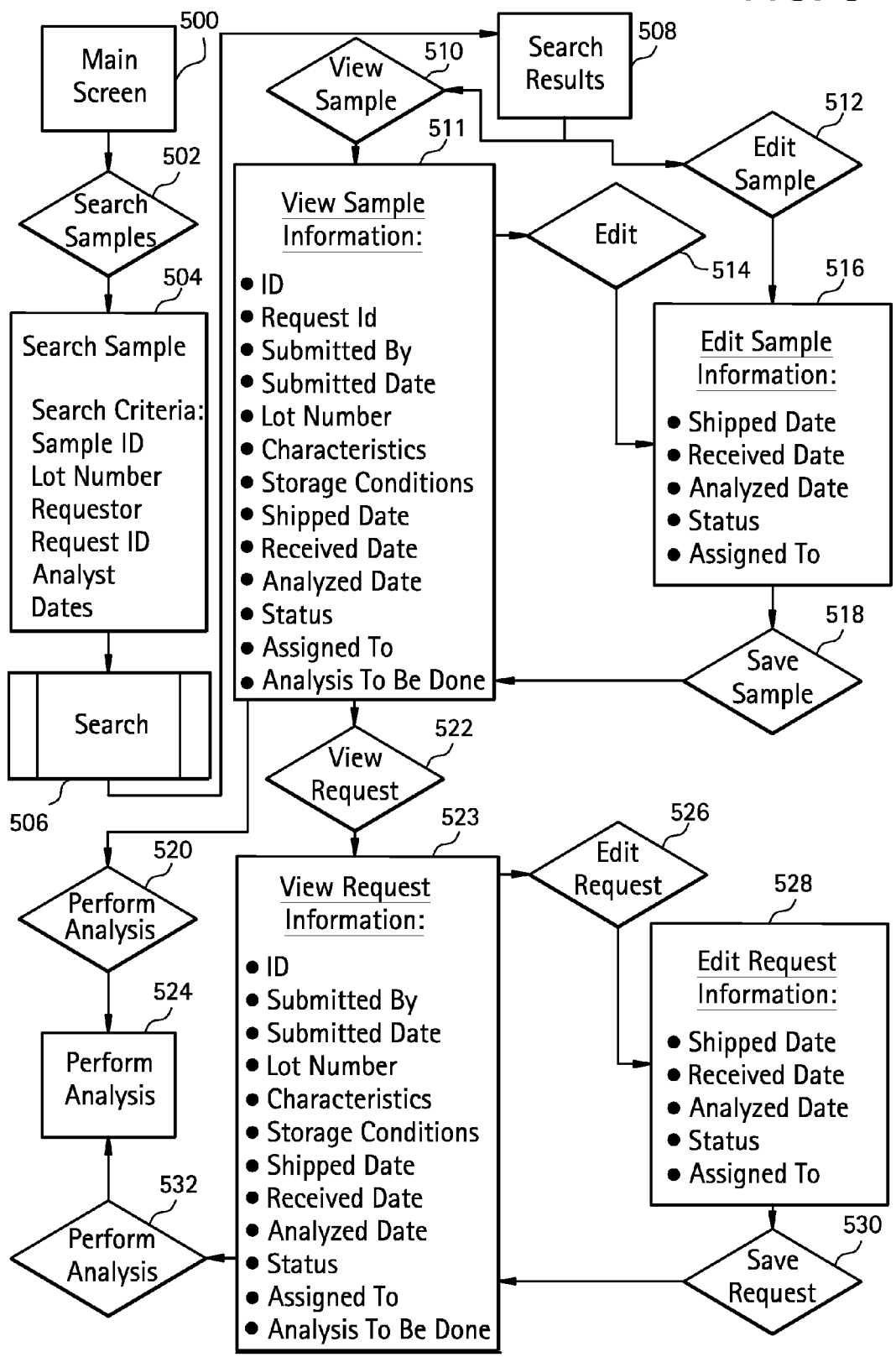
FIG. 5 depicts the process flow within the sample analysis and tracking module of a system in accordance with the present invention when a user selects to search samples.

FIG. 5 depicts the process flow within the sample analysis and tracking module of a system in accordance with the present invention when a user selects to search samples. Main screen 500 displays the function selections to the user. At step 502 the user selects to search samples. At step 504 the user enters one or more search criteria such as the sample identifier; the lot number, the requestor, the request identifier; the name of the analyst or the shipping date, the receipt date or the analysis date. At step 506 the system searches for the record or records that matches the search criteria and displays the search results to the user at step 508. The user may then select either to view the sample data or step 510 or to edit the sample data at step 512. If the user selects to view the sample then some or all of the following information is displayed at step 511: sample identification, name of submitter, date of submission, lot number, characteristics of the sample, storage conditions for the sample, shipping date, receipt data, analysis date, status, analyst assigned to the sample and a description of the analysis to be done on the sample. After review of the sample information the user may either decide to edit the sample information at step 514 or view the request at step 522. If the user selected to edit the sample information at either step 512 or step 514 the user may change one or more fields of the sample information: shipping date, received date, analysis data, status or analyst assigned. The sample information is then saved at step 518 and the modified sample information is displayed to the user at step 511. If the user selects the view the request at step 522 the review requests then some or all of the following information is displayed at step 523: sample identification, name of submitter, date of submission, lot number, characteristics of the sample, storage conditions for the sample, shipping date, receipt data, analysis date, status, analyst assigned to the sample and a description of the analysis to be done on the sample. After review of the request information the user may decide to edit request at step 526. If the edit request function is selected at either step 526 then the user is able to edit one or more of the following pieces of information at step 528: the shipping date, the received date, the analysis date, status or the analyst assigned to the sample. The edited request is then saved at step 530 and the edited request is displayed again at step 523. If the user selects the perform analysis function at either step 520 or step 532 then the system performs the analysis at step 524 in accordance with the process flow depicted in FIG. 9.

Figure 6:
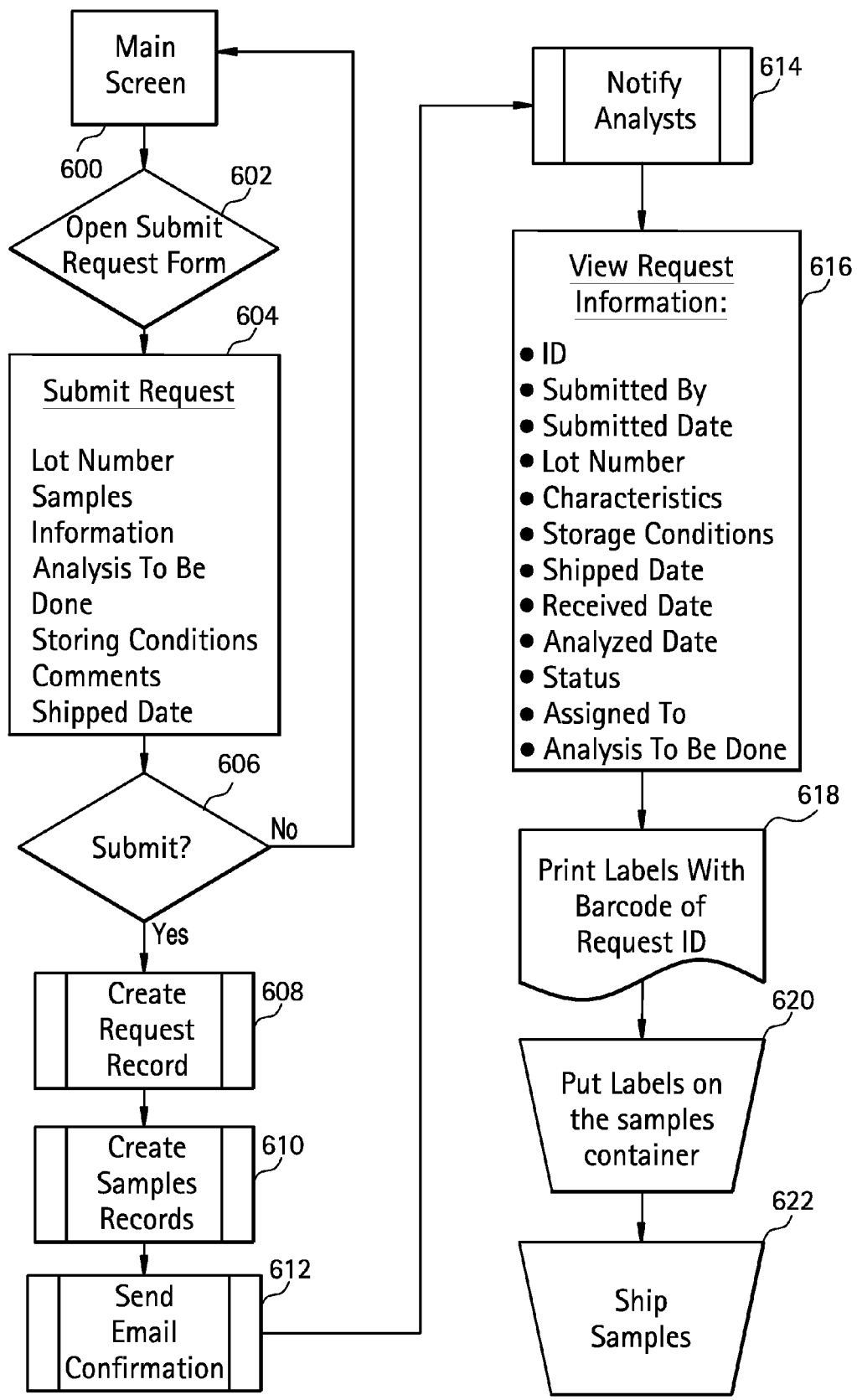
FIG. 6 depicts the process flow within the flow within the sample analysis and tracking module of a system in accordance with the present invention when a user selects to submit requests.

FIG. 6 depicts the process flow within the flow within the sample analysis and tracking module of a system in accordance with the present invention when a user selects to submit requests. At the main screen 600 the user selects to open a submit request form at step 602. The user is then asked to input the following data for the sample and the request: the lot number; sample information; analysis to be done; storage conditions; miscellaneous comments and the shipping date. If the user decides whether to submit the sample at step 606 then a request record is generated at step 606, a sample record is generated at step 610 and an e-mail confirmation is sent to the user at step 612. At step 614 an e-mail is sent to the assigned analyst to notify them of the submitted request. At step 616 the user verifies the information in the request including the following information: the identifier; the identification of the submitting party; the date submitted; the lot number; the characteristics of the sample; the storage conditions; the shipping date; the received date; the analysis date, the analyst assigned and a description of the analysis to be done. At step 618 labels are printed with a barcode of the request identifier. At step 620 the labels are affixed to the samples and the samples are shipped at step 622.

Figure 7:
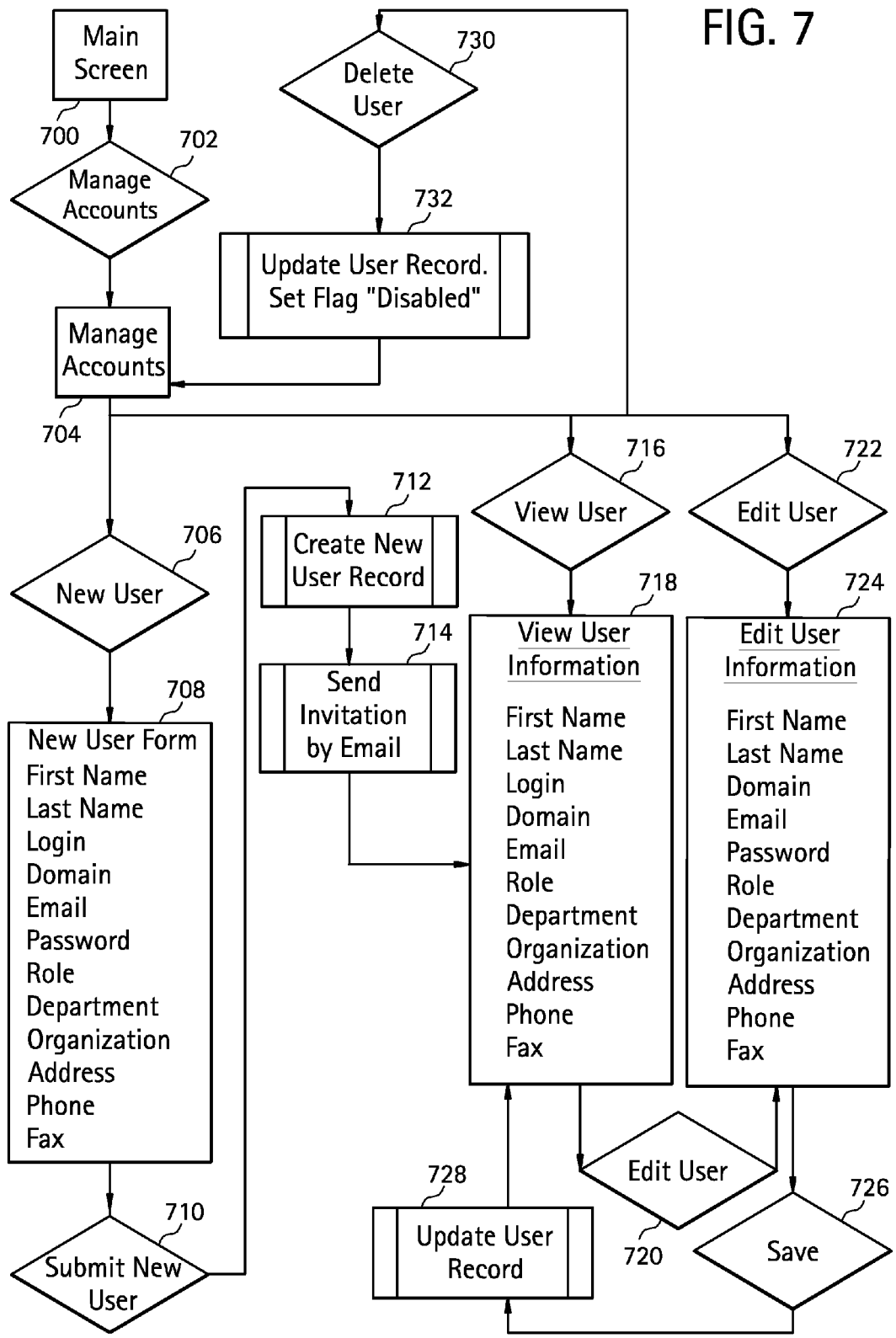
FIG. 7 depicts the process flow within the sample analysis and tracking module of a system in accordance with the present invention when a user selects to manage accounts.

FIG. 7 depicts the process flow within the sample analysis and tracking module of a system in accordance with the present invention when a user selects to manage accounts. At step 700 the user is presented with the option of managing accounts that can be selected at step 702. If the "manage accounts" function is selected the function begins at step 704 and the user is asked whether he or she desires to create a new user account at step 706, view user information at step 716, edit user information at step 722 or delete a user at step 730. If the user selects the creation of a new user at step 706 then the user is presented with a new user form for which the following fields should be completed: first name, last name, login, domain, e-mail, password, role, department, organization, address, phone number and fax number. The user completes this form, submits the form at step 710 and the system creates a new user at step 712. An e-mail message is sent to the new user at step 714 and the user is shown a view of the user information at step 718. This is the same step that is reached is the user selects the view user function at step 716. At step 718, the following information is displayed to the user: first name, last name, login, domain, e-mail, password, role, department, organization, address, phone number and fax number. The user can choose to edit the user information at step 720. If the user selects to edit at either step 720 or step 722 the user is permitted to edit the user information at step 724, the edited information is saved at step 726 and the user record is updated at step 728. The user is then shown the user information at step 718. If the user selects to delete the user at step 730, the user record is updated at step 732 to set the flag for the user to disabled and the user is retuned to the manage accounts screen at step 704.

Figure 8:
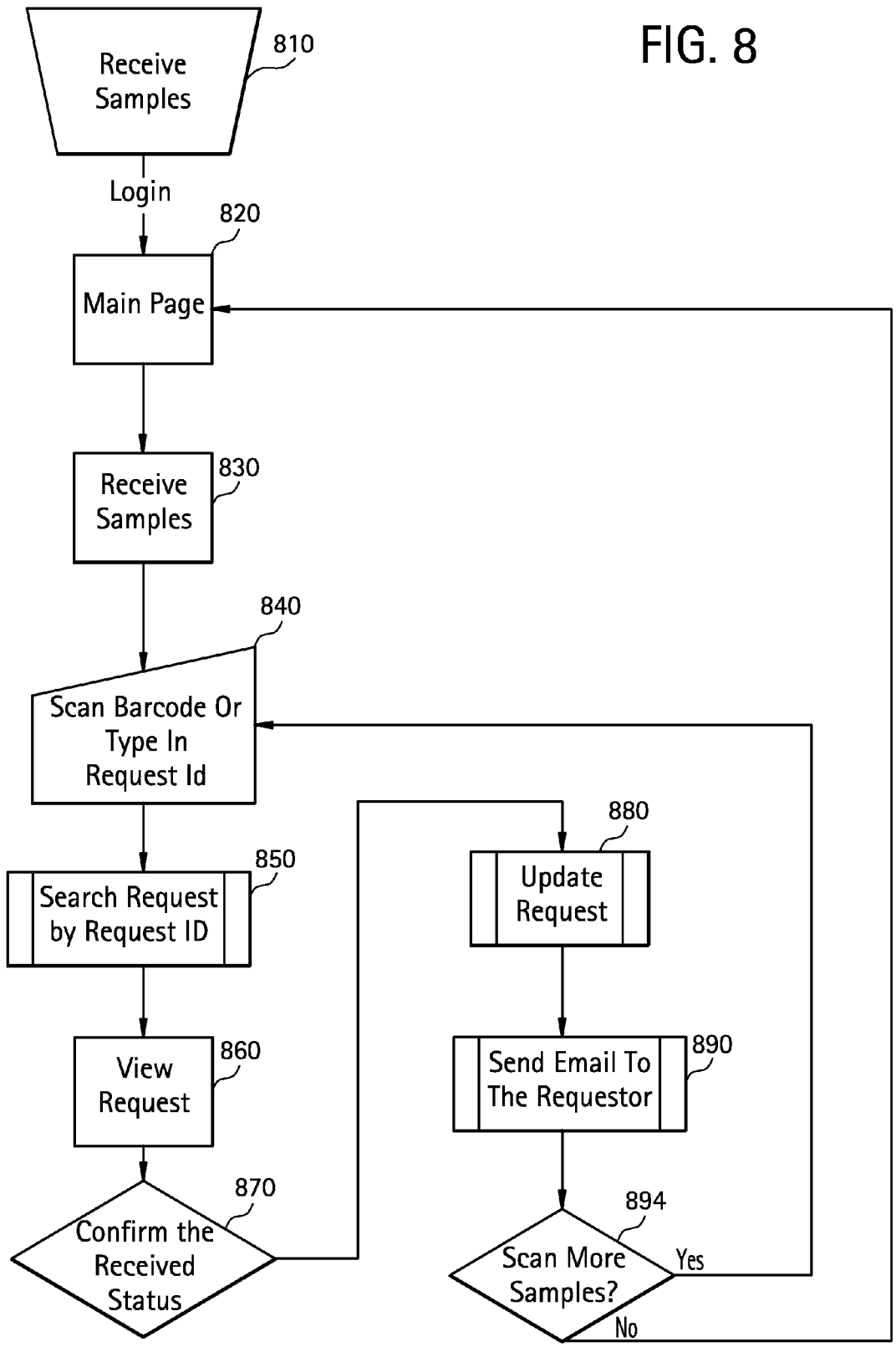
FIG. 8 depicts the process flow within the sample analysis and tracking module of a system in accordance with the present invention when a user selects to receive samples.

FIG. 8 depicts the process flow within the sample analysis and tracking module of a system in accordance with the present invention when a user selects to receive samples. At step 810 samples are physical received by the analyst 230. The analyst logs in to the sample and analysis tracking module and views the main page at step 820. The analyst selects the "receive samples" function at step 830 and is directed to scan the barcode that identifies the sample or to enter the request identifier into the system at step 840. At step 850 the database of samples is searched based on the request identifier and the request is viewed at step 860. The analyst confirms the received status for the samples at step 870 and the request is updated with the received date at step 880. At step 890 an e-mail is sent to the user/requestor to notify them of the receipt. At step 894 the analyst is queried as to whether there are more samples to scan. If there are more samples, the process returns to step 840. If there are no more samples to scan the main page is displayed again at step 820.

Figure 9:
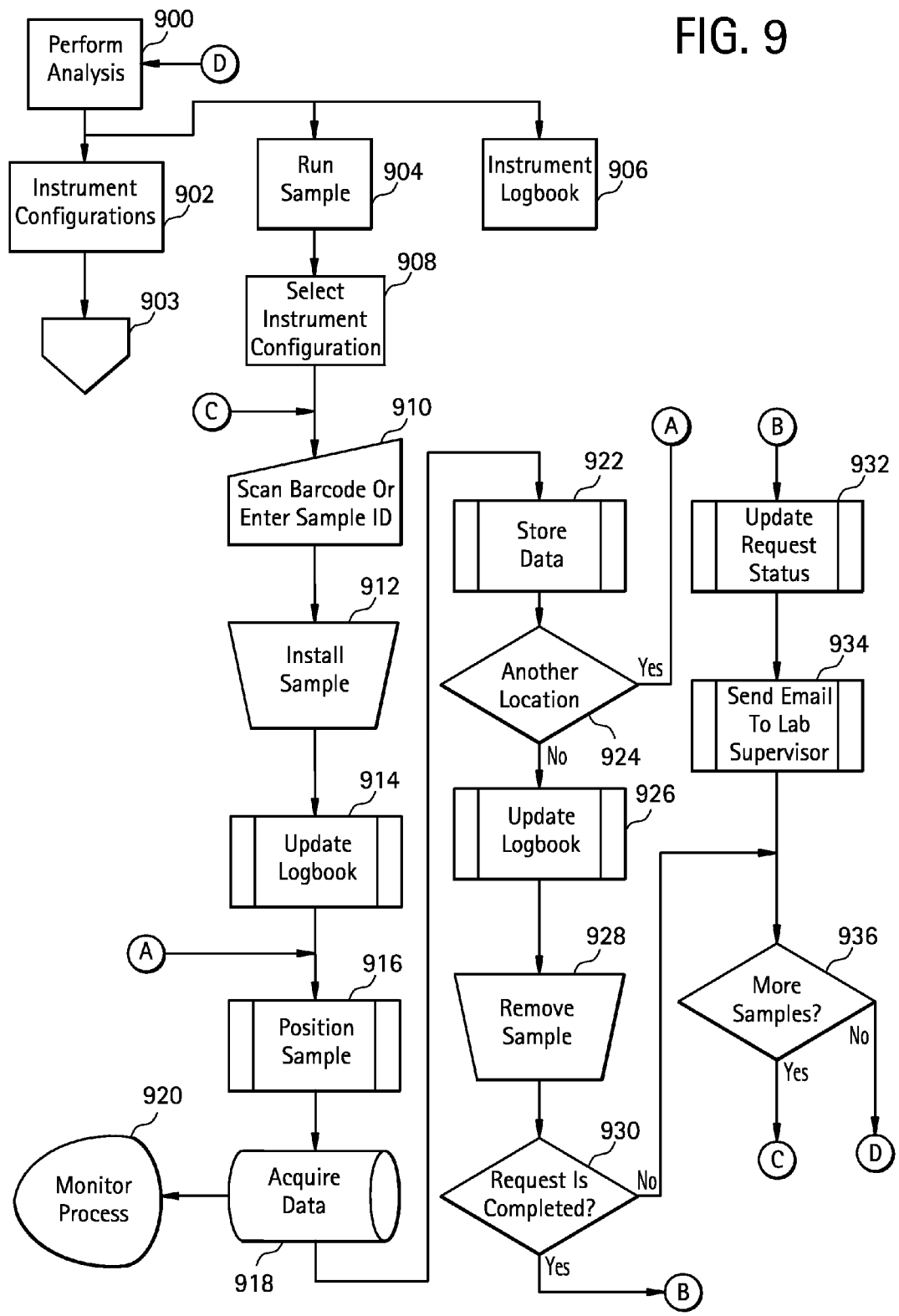
FIG. 9 depicts the process flow within the analysis processing module of a system in accordance with the present invention.

FIG. 9 depicts the process flow within the analysis processing module of a system in accordance with the present invention. At step 900 the analyst 230 begins performing analysis on a sample. If the instrument of the analysis processing module has not been configured then an instrument configuration function is performed at step 902 and the process branches to the FIG. 10 at step 903. If the instrument has been configured a sample may be run at step 904. At step 906 an entry is made in the instrument logbook to keep a record of the instrument settings used for the analysis. If a sample analysis is to be performed an instrument configuration appropriate for the sample is selected at step 908. The identification of the sample is input into the analysis processing module through either a barcode scanner or the entry of the sample ID into the module by the analyst at step 910. The sample to be analyzed is then installed by the analyst so that the instrument of the analysis processing module can take data from the sample at step 912. The logbook is updated with information on the sample at step 914. The sample is then positioned by the positioning device controller (discussed below with respect to FIG. 16). At step 916 and data is acquired at step 918. The analyst monitors the process at step 920 to insure that proper data is being acquired by the instrument of the analysis processing module. At step 922 the data is stored and the system asks whether additional data is desired at additional locations at step 924. If additional data is desired the process returns to step 916 to reposition the sample. If no additional data is desired the logbook is updated at step 926 and the sample is removed by the analyst at step 928. The system queries the analyst as to whether the request is complete at step 930 and if it is the status of the request is updated to "complete" at step 932 and an e-mail is sent to the lab supervisor at step 934. If the request is not complete the process asks the analyst whether there are more samples and if there are returns the process to step 910 where the barcode of the next sample is scanner or the ID of the sample is entered into the system by the analyst. If the there are no more samples the process returns to step 900.

Figure 10:
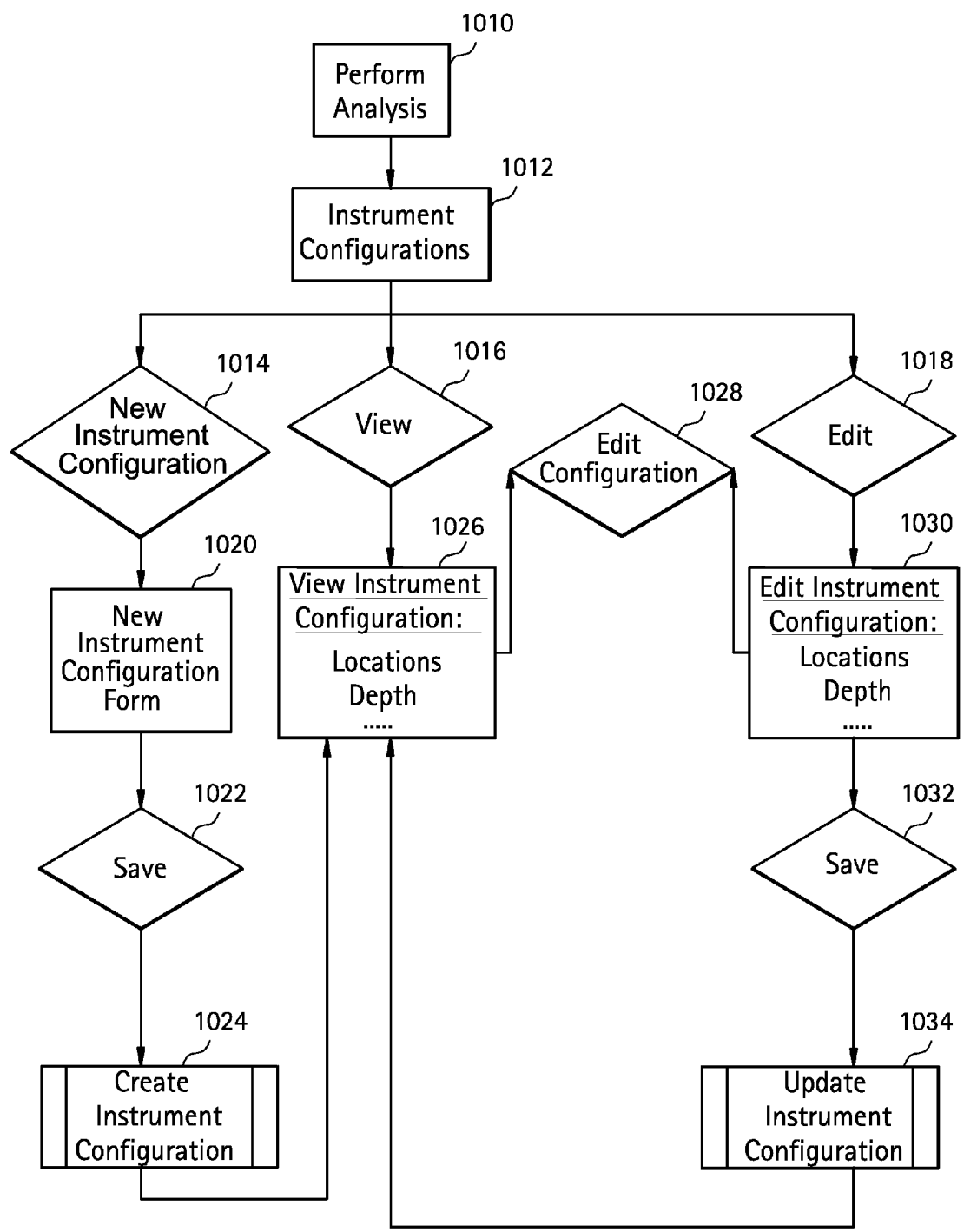
FIG. 10 depicts the process flow for instrument configuration within the analysis processing module of a system in accordance with the present invention.

FIG. 10 depicts the process flow for instrument configuration within the analysis processing module of a system in accordance with the present invention. If instrument configuration is necessary before a sample can be analyzed the following process begins at step 1010 where instrument configurations are initialized at step 1012. The system queries the analyst whether the configuration is for a new instrument at step 1014. If it is then the new instrument configuration form is presented to the analyst for completion at step 1020. The contents of the form will depend on the instrument being configured. At step 1022 the new instrument configuration form is saved and the system creates an instrument configuration for the instrument at step 1024. At step 1026 instruments configurations can be viewed. The analyst may reach this point either by creating a new instrument configuration or selecting "view" in the instrument configuration menu at step 1016. Through either step 1018 or step 1028 the analyst may choose to edit an instrument configuration. At step 1018 the analyst has selected to edit an instrument configuration that is then displayed to the user at step 1030 in a format that may be edited by the analyst. At step 1032 the edited instrument configuration is saved and the instrument configuration is updated at step 1034. Upon updating the instrument configuration the analyst is returned to the view function at step 1026. Using this set of menus and process flow the analyst is able to enter new instrument configurations, view existing configurations and edit them.

Figure 11:
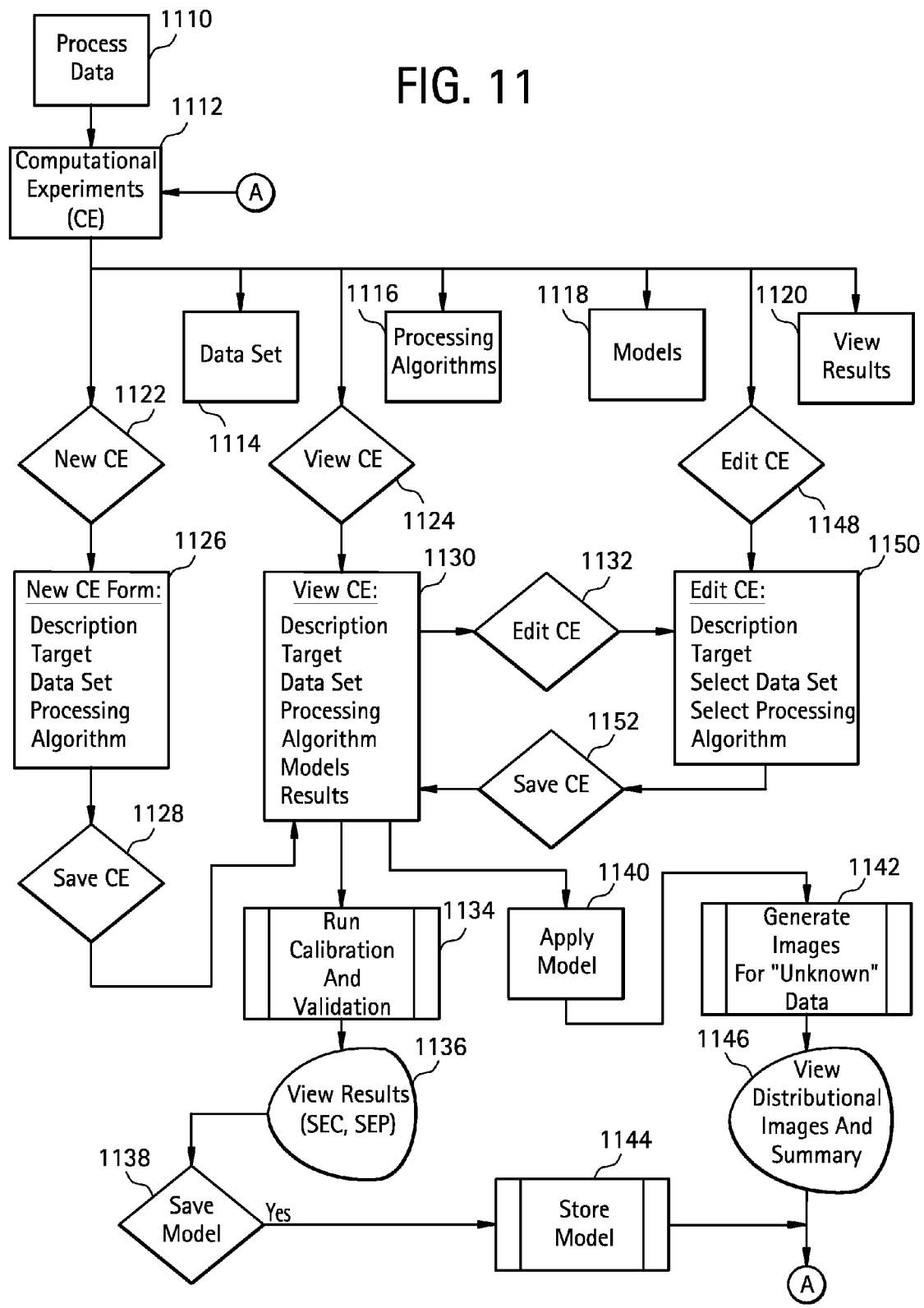
FIG. 11 depicts the process flow in the data processing module of a system in accordance with the present invention.

FIG. 11 depicts the process flow in the data processing module of a system in accordance with the present invention. At step 1110 the processing of data in the data processing module begins with the initialization of computational experiments (CE) by the analyst at step 1112. The analyst may select to perform a new computational experiment (step 1122), view computation experiments (step 1124) or edit existing computational experiments (step 1148). The analyst may also have access to the data set at step 1114, the processing algorithms at step 1116, the models at step 1118 or the results at step 1120. If the analyst chooses to initiate a new CE at step 1122 the new CE form is presented to the analyst at step 1126 which requests the analyst to input a description of the CE to be performed, the target, the data set, and the processing algorithm to be used. The CE is saved at step 1128 and viewed at step 1130, which is also the step at which the analyst arrives if he or she selects to view a CE at step 1124. After viewing the CE at step 1130 the computational experiment is run at step 1134 to perform calibration and validation. The results are viewed at step 1136 and a choice to save the model is made at step 1138 and the model is stored at step 1144. At step 1140 the stored model is applied to the data and an images is generated for "unknown" data at step 1142. The distributional images and a summary of the results of the application of the model can be viewed at step 1146. After both steps 1144 and 1146 the system returns to the main screen for performing computational experiments at step 1112. If the analyst either selects to edit a CE at step 1148 or, after viewing, at step 1132, the analyst is presented with a screen to edit the description target, data set, and processing algorithm used in the CE at step 1150. The modified CE can be saved at step 1152 and the process returns to the view function at step 1130.

Figure 12:
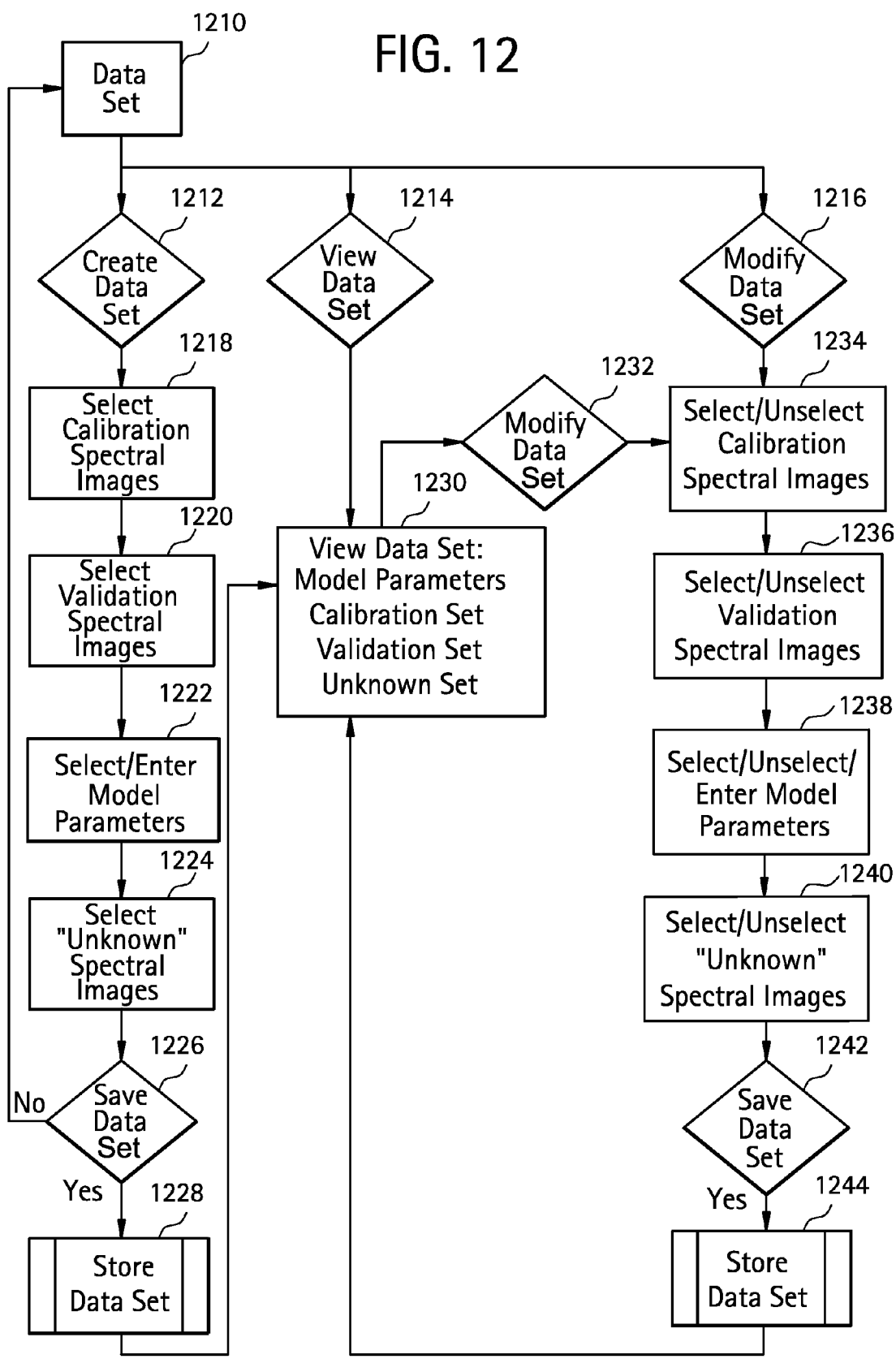
FIG. 12 depicts the process flow for creating, viewing and modifying the data set in the analysis processing module of a system in accordance with the present invention.

FIG. 12 depicts the process flow for creating, viewing and modifying the data set in the analysis processing module of a system in accordance with the present invention. The creation, viewing and modification of data sets are accomplished using the process of FIG. 12 which is initialized at step 1210. At step 1212 the analyst may create a data set by selecting the calibration spectral images at step 1218, selecting the validation spectral images at step 1220, selecting and entering parameters for a model at step 1222 and selecting "unknown" spectral images at step 1224. The analyst can choose to save the data set at step 1226. If the analyst chooses to save the data set it is stored at step 1228, if not, the process returns to the main data set screen at step 1210 without saving the data set. At step 1214 the analyst can select to view the data set and the system displays the data set at step 1230 including the model parameters, the calibration set, the validation set and the unknown set. The analyst may select to modify the data set after viewing at step 1232 or prior to viewing at step 1216. At step 1234, the analyst may select or unselect the calibration spectral images. At step 1236, the analyst may select or unselect the validation spectral images. At step 1238 the analyst may select, unselect or enter model parameter. At step 1240 the analyst may select or unselect "unknown" spectral images. Once these selections are completed the analyst may choose at step 1242 to save the modified data set, which is then stored at step 1244.

Figure 13:
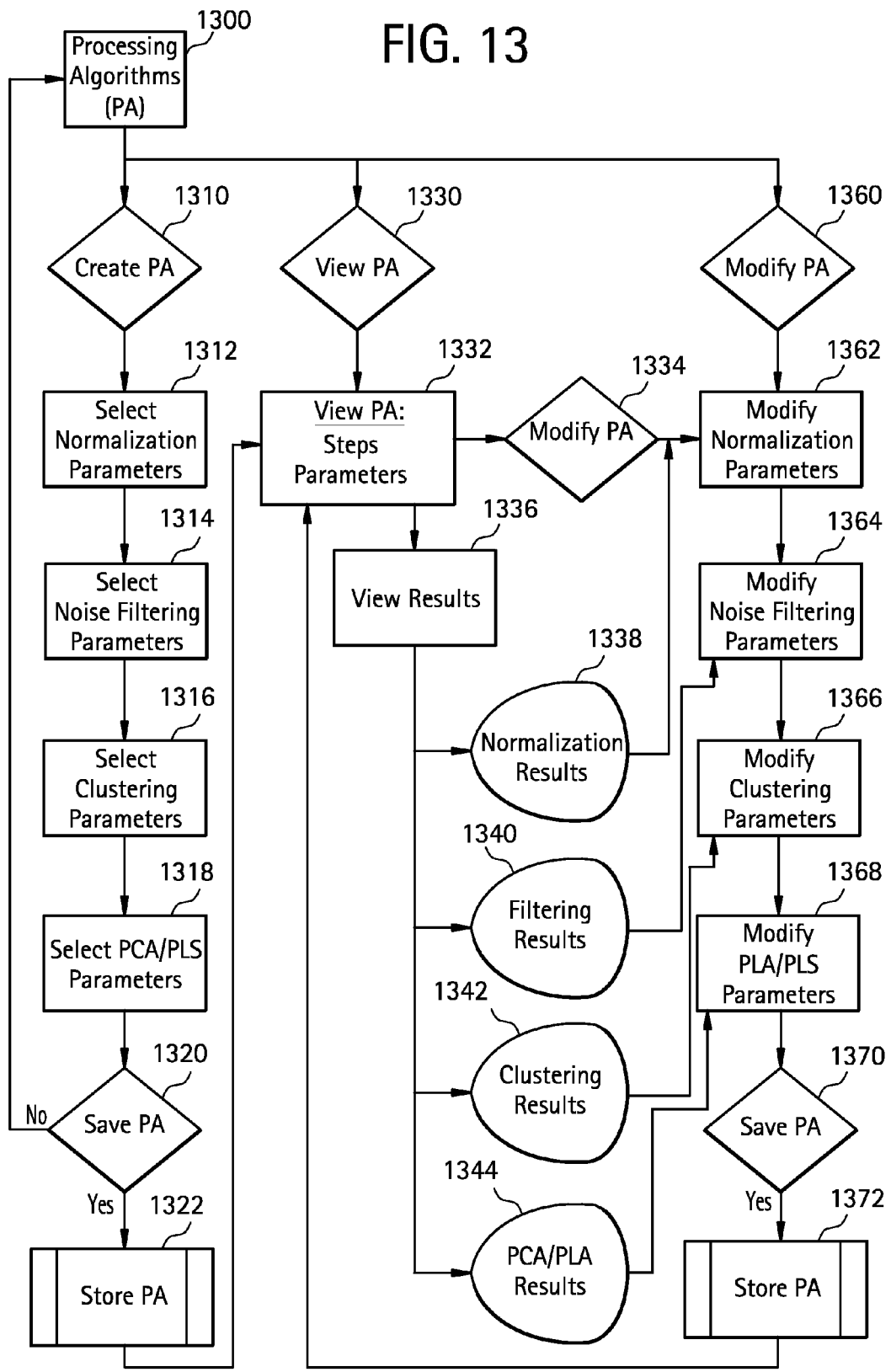
FIG. 13 depicts the process flow for configuring processing algorithms in the data processing module of a system in accordance with the present invention.

FIG. 13 depicts the process flow for configuring processing algorithms in the data processing module of a system in accordance with the present invention. The data processing module performs three primary functions: creation of a processing algorithm (PA); viewing of a processing algorithm and modification of a processing algorithm. At step 1300 the process is begun. Creation of a processing algorithm is begun at step 1310. The first step in creation of the processing algorithm is the selection of normalization parameters at step 1312. At step 1314 the parameters of the noise filtering algorithm are selected by the module. At slop 1316 the parameters for the clustering algorithm are selected. At step 1318 the parameters for the multivariate analysis (PCA/PLS) are selected. At step 1320 the processing algorithm may be saved and at step 1322 it is stored in the system database 140. At step 1330 the process for viewing the processing algorithm are initiated and the algorithm is viewed by the analyst at step 1332. At step 1336 the results of the application of the processing algorithm are viewed including the normalization results at step 1338, the filtering results at step 1340, the clustering results at step 1342 and the PCA/PLS results at step 1344. At step 1334 and at step 1360 a decision whether to modify the processing algorithm may be made based on the viewed results. The normalization parameters can be modified at step 1362. The noise filtering parameters can be modified at step 1364. The clustering parameters can be modified at step 1366 and the PCA/PLS can be modified at step 1368. At step 137U the decision is made whether to store the processing algorithm, which is stored in the system database 140 at step 1372.

Figure 14:
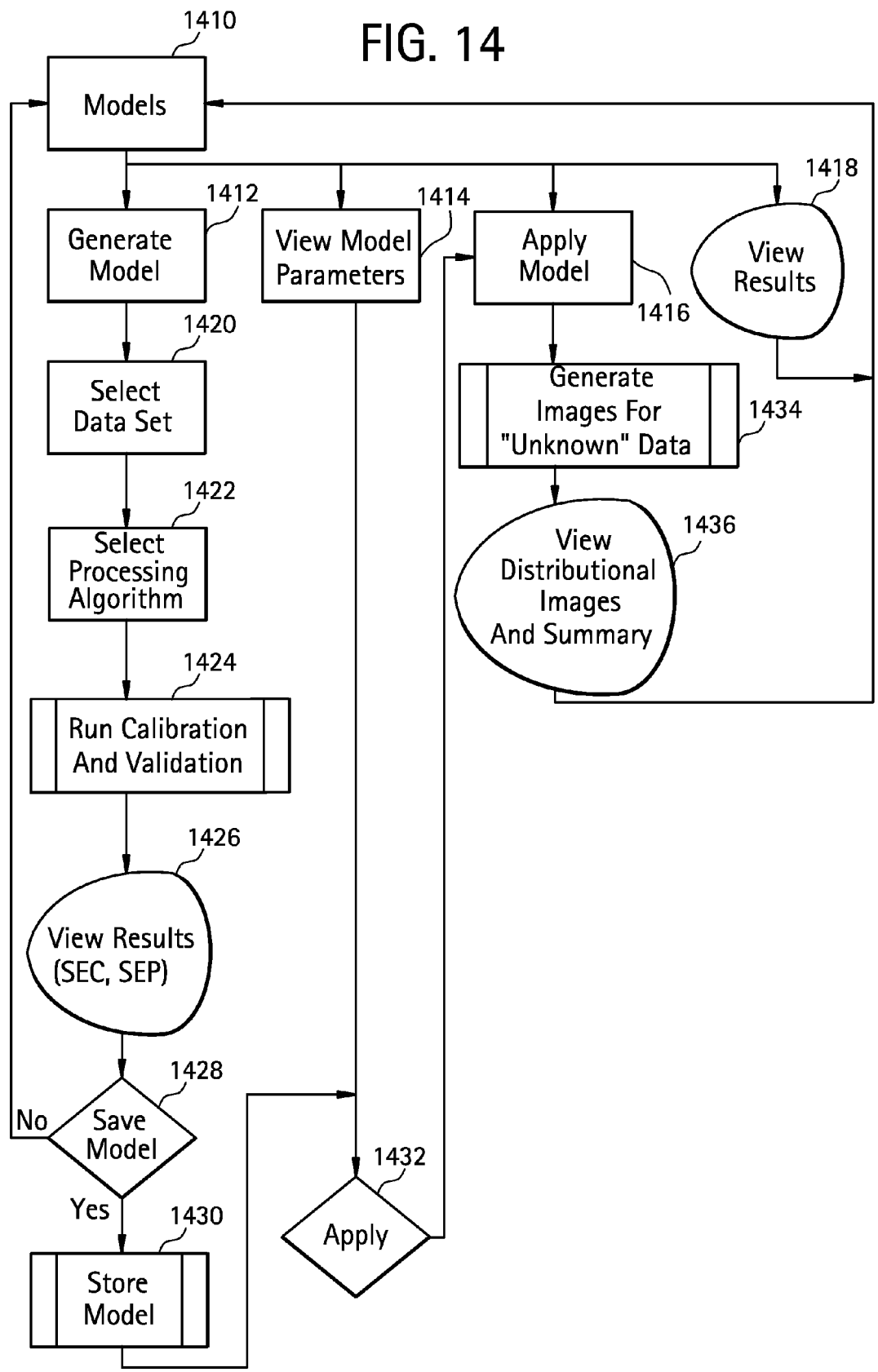
FIG. 14 depicts the process flow for generating and applying models in the data processing module of a system in accordance with the present invention.

FIG. 14 depicts the process flow for generating and applying models in the data processing module of a system in accordance with the present invention. The process is begun at step 1410 from which the analyst may select to generate models at step 1412, view model parameters at step 1414, apply a model at step 1416 or view results at step 1418. If generation of a model is selected by the analyst, then a data set is selected at step 1420, a processing algorithm is selected at step 1422 and the calibration and validation function is run at step 1424. Results are viewed at step 1426 and the analyst may choose to save the model at step 1428 which results in storing the model at step 1430. If the model is stored at step 1430 or the analyst selects to view model parameters at step 1414 the model may then be applied at step 1432 which results in applying the model at step 1416. In applying the model, images are generated for "unknown" data at step 1434 and distributional images and summary information are viewed by the analyst at step 1436. After viewing results at step 1418 or viewing distributional images and summary at step 1436, the process returns to the start at step 1410.

Figure 15:
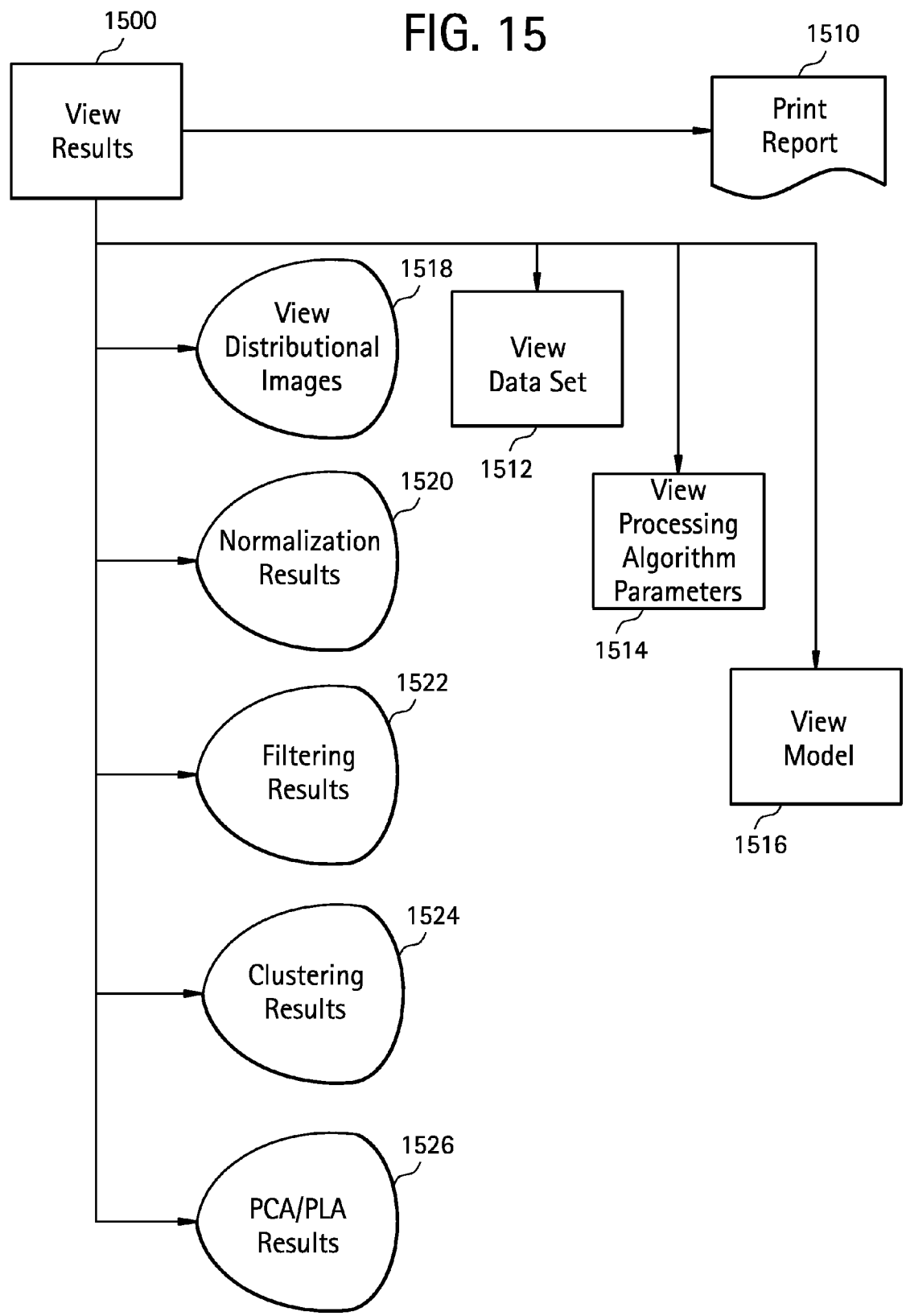
FIG. 15 depicts the process flow for viewing results in a system in accordance with the present invention.

FIG. 15 depicts the process flow for viewing results in a system in accordance with the present invention. The result viewing function begins at step 1500 at which time the analyst, lab supervisor or requestor/user can view distributional images (step 1518), normalization results (step 1520), filtering results (step 1522), clustering results (step 1524) and PCA/PLS results (step 1526). The data set may also be viewed at step 1512. The processing algorithm and its parameters can be viewed at step 1514 and the model can be viewed at step 1516. If desired a report can be printed at step 1510.

Figure 16:
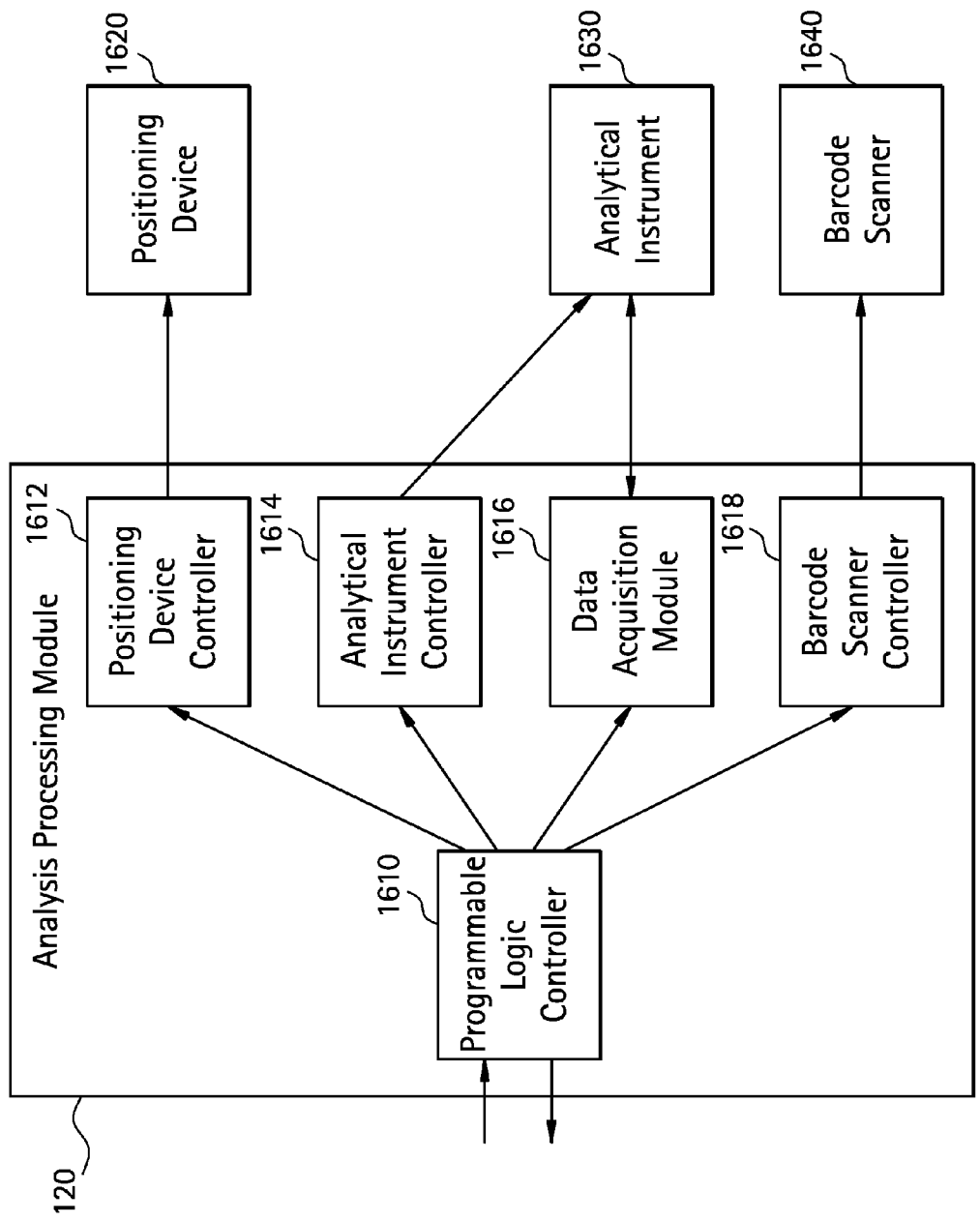
FIG. 16 depicts a schematic of the analysis processing module of a system in accordance with the present invention.

FIG. 16 is a schematic diagram of the analysis processing module 120 of FIG. 1 and connected peripheral devices. Analysis processing module 120 comprises a programmable logic controller (PLC) 1610 (such as the model T100MD2424+PLC from Triangle Research International, Inc.) with a positioning device controller 1612. Positioning device controller 1612 sends control signals to the positioning device 1620 that controls the position of the sample in relation to the analytical instrument 1630. Programmable logic controller 1610 is also in communication with an analytical instrument controller 1614 that sends control signals to the analytical instrument 1630 in order to control the function of the analytical instrument during the analysis of a sample. Information regarding the settings of the analytical instrument is also sent to the analysis processing module and may include the type of instrument, the sample position, the number of observations and the types of data collected. Programmable logic controller 1610 is also in communication with a data acquisition module 1616 that collects data from the analytical instrument 1630 in response to the generation of test and analysis data during the analysis of a sample. Programmable logic controller 1610 is also in communication with a barcode scanner controller 1618 that sends control signals to a barcode scanner 1640 that is used to read barcodes placed on or near samples under analysis.

The analysis processing module 120 may be housed in one unit or may be comprised of several units in communication with one another. The positioning device 1620 is custom designed for the object of interest. WITec Instruments, Savoy, Ill. sells a stent positioning device. The analytical instrument 1630 may be a confocal Raman microscope such as the CRM200 microscope system from WITec Instruments Corporation (Savoy, Ill.) or other non-destructive analysis tool such as the FluoView™confocal fluorescence microscope from Olympus from or generic polarized light or phase microscopes offered by Zeiss, Olympus and Nikon. Barcode scanner 1640 can be any commercially available barcode scanner such as the Wasp Bar Code scanner from Wasp Bar Code Technologies. The barcode scanner 1640 could also be replaced with any other means of automatically identifying a sample such as RFID tags or other such means.

Figure 17:
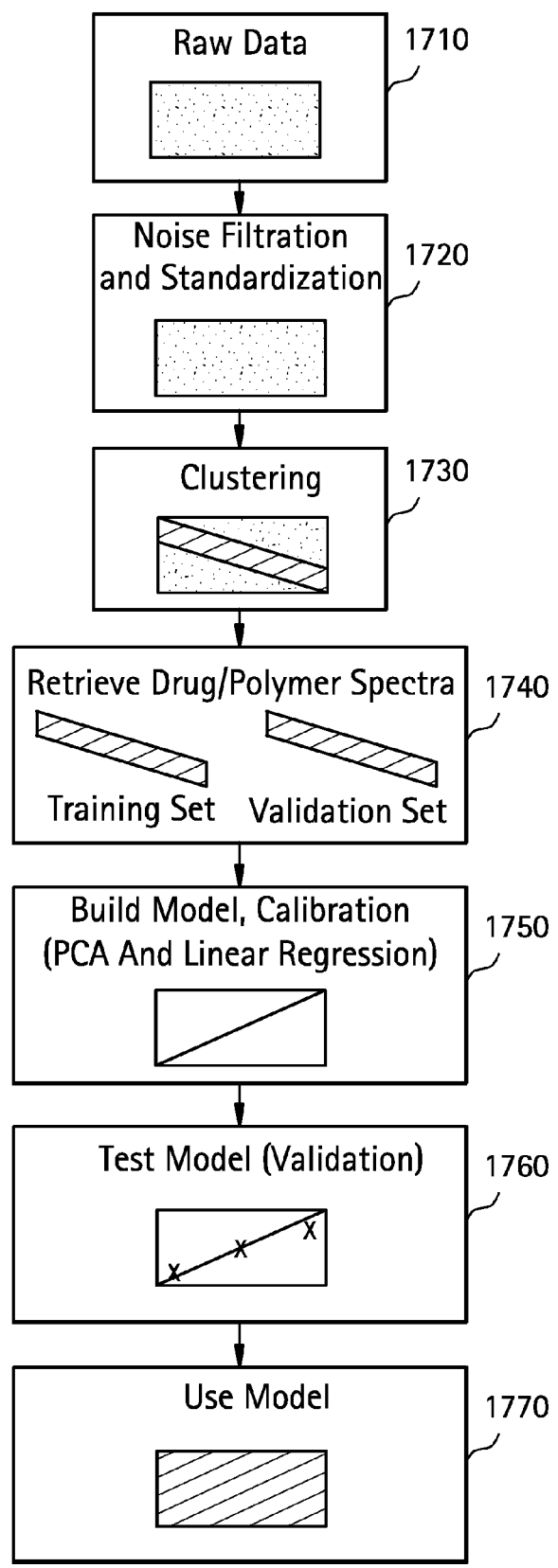
FIG. 17 depicts a high-level flow diagram for the processing of confocal Raman microscopy data within the data processing module of a system in accordance with the present invention.

FIG. 17 is a high-level flow diagram depicting the flow of information in the data processing module of a system in accordance with the present invention. At step 1710 raw data is sent to the data processing module 130 by the sample and analysis tracking module 110 for processing. At step 1720 the raw data is pre-processed using a filter to remove noise and the data is standardized. The type of data filtration and standardization necessary will depend on the type of raw data being provided. For example, a band-pass filter is used to exclude the laser line at the detector when Confocal Raman microscope is used. At step 1730 a clustering algorithm is used to identify the regions of interest and separate from the noise. The preferred clustering algorithm is K-means although other partitional clustering algorithms such as QT-clustering or c-means clustering may also be used. Other clustering strategies include neural networks, or spectral clustering. At step 1740 the training set and validation set for a specific type of test sample is retrieved from the system database 140. In order to perform the analysis for a specific sample training sets and validation sets must be developed for the sample type. For example, in a system for analyzing the coatings on drug-eluting stents, it would be necessary to generate a training set and a validation set for each combination of active ingredient and polymer in order to correctly identify the components and their respective concentrations. The generation of training sets and validation sets is discussed below. At step 1750 quantitative and qualitative analyses are performed by building a model and calibrating the model using calibration standards and PCA/PLS or simple linear regression. The model is tested at step 1760 in order to validate the model and then the model is used to generate a visualization at step 1770 for output to the user.

One embodiment of the system utilizes a CRM microscope as the analytical instrument 1630 to analyze drug-eluting stents. Positioning device 1620 is a sample holder that allows for x,y and rotational translation. The sample identity and date of fabrication of each sample stent is input into the sample and analysis tracking module 110 and is stored in the system database 140 in accordance with the sample set name. Data collected by the analysis processing module 120 is a series of xz spectral images containing 4800 spectra. The data processing module 130 is used as described above to process the collected data. The noise filtration and normalization step filters by spectrum maximum and reduces interference from cosmic rays and fluorescence. Each file of 4800 spectra with 1024 points per spectra is filtered to exclude the Rayleigh line (first 150 points). Normalization is performed according to the following equation (1) where $z_i$ is the normalized value and $x_i$ is the source value:

$$z_i = \frac{x_i - \min(x_i)}{\max(x_i) - \min(x_i)} \tag{1}$$

The global minimum and maximum values are used for the normalization. Otherwise, a normalized spectrum for air or metal looks like a random value from 0 to 1 Next, the cosmic rays are removed from the data by setting a threshold value. Values above the threshold were considered cosmic rays and the value at this point was changed to the averages of the values of the neighboring intensities. Fluorescence was also filtered from the data by setting a width threshold value for hands observed in the spectra. If the width was greater than 630 $cm^{-1}$ it was considered to contain fluorescence and was excluded. Finally to identify the most informative factors, 5 regions within the spectra were identified as the most informative by comparing to pure component spectra and responses to changes in concentration. The data processing module 130 identifies the relevant spectra for analysis using K-means clustering. The clusters that resulted were manually defined as to which cluster belonged to the API/polymer layer. The spectra that were selected by cluster analysis were then used in a principle component model to build a model for API concentration.

The above strategy was used to quantify the API content for a drug-eluting stent. For each quantitative method (such a determination of API content), it is necessary to generate a series of standards containing variable amounts of both API and matrix components The standards are analyzed via the instrumental method (i.e. Confocal Raman Microscopy). This data is then used to build a calibration model. To validate the calibration model, a second set of samples is required. The number of samples can be increased to improve the accuracy and precision of the calibration model. Once a specification is set upon the model, the model can be validated and put into use. The final step involves a series of unknown samples. The model determines and visualizes the distribution of API and matrix components.

The above system has been implemented in an embodiment designed to analyze sirolimus coated drug-eluting stents in which sirolimus and a polymer or polymers are applied to a metal substrate. The following describes tests performed on the CRIVI-based system and its use to analyze such stents in order to show its accuracy.

First, a set of sample stents was created to test the system, sirolimus, poly (ethylene-co-vinyl acetate) [PEVA] and poly (n-butyl methacrylate) [PBMA] were applied to stents. Additionally, Poly (o-chloro-p-xylylene) [parylene-C] was deposited onto 6 cell by 37 mm L605 alloy stents before application of the drug-polymer coating. A series of solutions containing sirolimus, PEVA and PBMA were prepared in THF and spray-coated onto the stents. The mass of each individual stent was recorded before and after spraying to obtain the total stent coating mass. An experimental mixture design was used to determine the formulations studied. Table 1 summarizes the composition of the solutions that were spray-coated onto stents. A target weight of $1\times10^3$ µg of each formulation was applied on the stents. A limited number of formulations were also spray-coated onto planar parylene-C pretreated L605 alloy substrates. After spray coating, a selected number of the stents from each formulation were sterilized before CRM and high-performance liquid chromatography (HPLC) analysis. The independent test samples to test the component quantitative models were prepared on pretreated parylene-C 7 cell by 33 mm stainless steel stents. A target weight of $1.5\times10^3$ µg of a formulation containing 28.4, 28.4, and 43.2 wt % sirolimus, PEVA, and PBMA were prepared to test the quantitative models.

TABLE 1

Polymer/drug Formulations Spray-coated onto Stents and Planar Substrates.

| Group | API wt % | PEVA wt % | PBMA wt % |
|---|---|---|---|
| A | 5.0 | 90.0 | 5.0 |
| B | 5.0 | 5.0 | 90.0 |
| C | 5.0 | 38.7 | 56.3 |
| D | 29.0 | 67.0 | 4.0 |
| E | 29.0 | 3.7 | 67.3 |
| F | 29.0 | 29.0 | 42.0 |
| G | 50.0 | 47.0 | 3.0 |
| H | 50.0 | 2.6 | 47.4 |
| I | 50.0 | 20.4 | 29.6 |
| J | 29.0 | 16.5 | 54.5 |
| K | 29.0 | 41.5 | 29.5 |
| L | 39.5 | 18.0 | 42.5 |
| M | 14.5 | 50.5 | 35.0 |
| N | 100.0 | 0.0 | 0.0 |
| O | 0.0 | 1000.0 | 0.0 |
| P | 0.0 | 0.0 | 100.0 |

Confocal Raman Microscopy. Spectral depth profiles of the samples were performed with a CRM200 microscope system from WITec Instruments Corporation (Savoy, Ill.). The instrument was equipped with a Nd: YAG frequency doubled laser (532 nm excitation), a single monochromator (Acton) employing a 600 groove/mm grating and a thermoelectrically cooled 1024 by 128 pixel array CCD camera (Andor Technology). The microscope was equipped with appropriate collection optics that included a holographic laser bandpass rejection filter (Kaiser Optical Systems Inc.) to minimize Rayleigh scatter into the monochromator. The Raman scattered light was collected with a 50 µm optical fiber. Using the "Raman Spectral Imaging" mode of the instrument, spectral images were obtained by scanning the sample in the x, z direction with a piezo driven xyz scan stage and collecting a spectrum at every pixel. Typical integration times were 0.3 s per pixel. The spectral images were 4800 total spectra corresponding to a physical scan dimension of 40 by 20 µm. For presentation of the confocal Raman data, images are generated based on unique properties of the spectra (i.e. integration of a Raman band, band height intensity, or band width). The microscope stage was modified with a custom-built sample holder that positioned and rotated the stents around their primary axis. The x direction is defined as the direction running parallel to the length of the stent and the z direction refers to the direction penetrating through the coating from the air-coating to coating-metal interface. Typical laser power was less than 10 mW on the sample stage. All experiments were conducted with a plan achromat objective, $100\times N_A = 0.9$ (Nikon).

One sterile and one nonsterile stent from each formulation group were analyzed. An additional three sterile stents were analyzed from Groups C, F, and I of Table 1. For each stent, three locations were selected along the length. The three locations were located within one-third portions of the stents so that the entire length of the stent was represented in the data. The stent was then rotated 180° around the circumference and an additional three locations were sampled along the length. In each case, the data was collected from the strut portion of the stent. Six random spatial locations were profiled on the coated planar substrates. The Raman spectra of each individual component present in the formulation were also collected for comparison and reference. Using the instrument software, the average spectra from the spectral image data were calculated by selecting the spectral image pixels that were exclusive to the active drug-polymer layer. The average spectra were then exported into GRAMS/AI v. 7.02 software (Thermo Galactic) and the appropriate Raman bands were fit to a Voigt function. The band areas and shift positions were recorded.

The pure component spectrum for each component was also collected at 532 nm and 785 nm excitation. The 785 nm excitation spectra were collected with a confocal Raman microscope (WITec Instruments Corporation Savoy, Ill.) equipped with a 785 nm diode laser, appropriate collection optics, and a back-illuminated thermoelectrically cooled 1024 by 128 pixel array CCD camera CCD camera optimized for visible and infrared wavelengths (Andor Technology).

Drug Content Method. The total amount of sirolimus present in units of micrograms per stent was determined by reverse phase high performance liquid chromatography with UV detection (RP-HPLC-UV). The analysis was performed with a modification of literature-based HPLC methods for sirolimus. The average drug content of five sterile and five non-sterile stents from each formulation was reported. In addition, individual stent drug content was performed on stent samples after confocal Raman measurements were completed.

ATR-FTIR Method. A Thermo Nicolet 6700 Fourier Transform infrared (FTIR) equipped with diamond single-bounce attenuated total reflectance (ATR) accessory analyzed five unique formulations present on planar substrates. Typical acquisition was 32 scans with a resolution of 4 $cm^{-1}$. The aperture was set to 100 µm. A total of six random locations per sample were analyzed. The spectra were imported into GRAMS software and the appropriate peak areas were calculated.

Raman Spectroscopy. There are three components that constitute the CYPHER® Stent drug-polymer coating, sirolimus and the two polymers PEVA and PBMA. Differential scanning calorimetry and atomic force microscopy data reveals the two polymers are immiscible on the micrometer to sub-micrometer length scale. The stent drug-polymer coating is considered to be an immiscible ternary blend on this length scale. The primary focus for this work was to develop a quantitative model to describe each of these components because it would be applicable to describe the distribution of components found in CYPHER® Stent as well as other drug-coated stent product lines. Because this coating is heterogeneous, we spatially sampled an area much larger than the domains present within the coating. To be useful for chemical mapping, the component of interest must possess a unique spectral signature that would scale with its respective concentration. The concentration is related to the Raman analytical signal, I, by the relationship:

$$I = kC$$

where k represents a complex constant of instrument and sample parameters and C is the concentration of analyte. The analytical signal should therefore be directly proportional to the concentration.

Figure 18A:
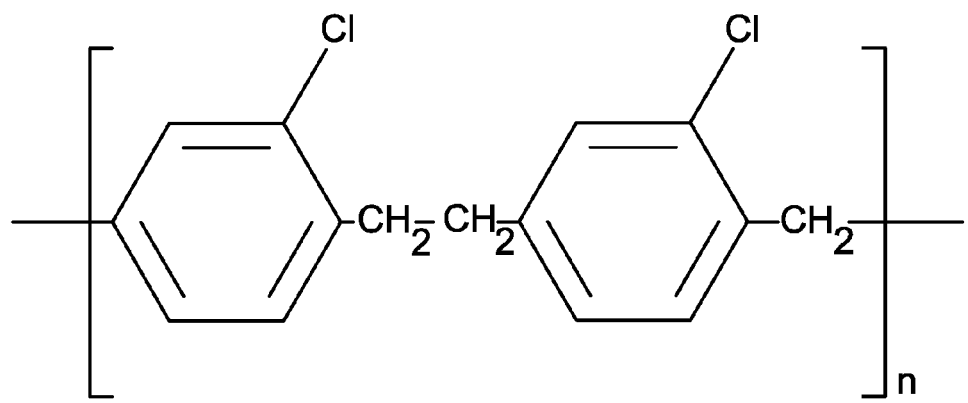
FIGS. 18*a-d* depicts the chemical structures for each component of a drug-eluting stent being analyzed in accordance with the present invention.
Figure 18B:
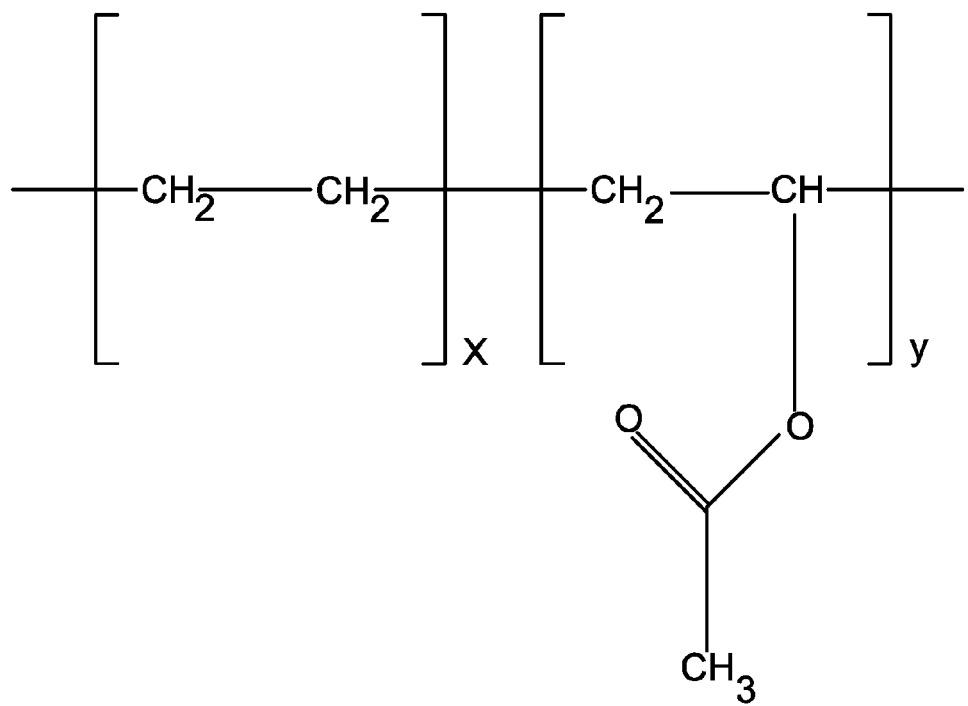
Figure 18C:
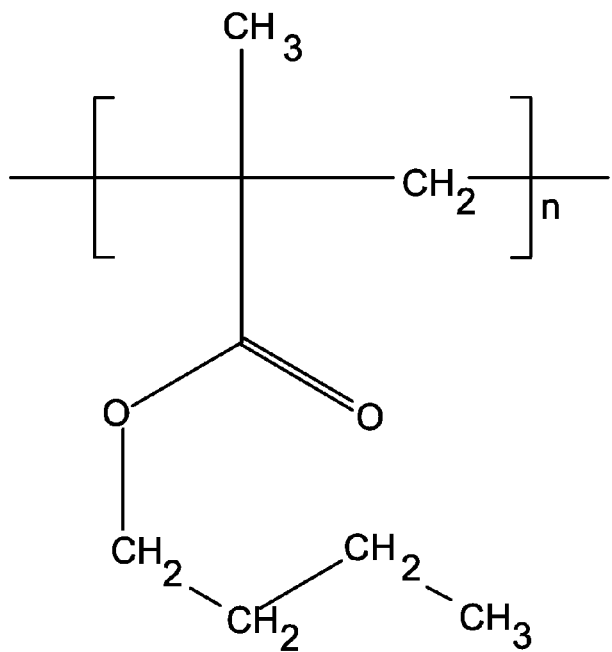
Figure 18D:
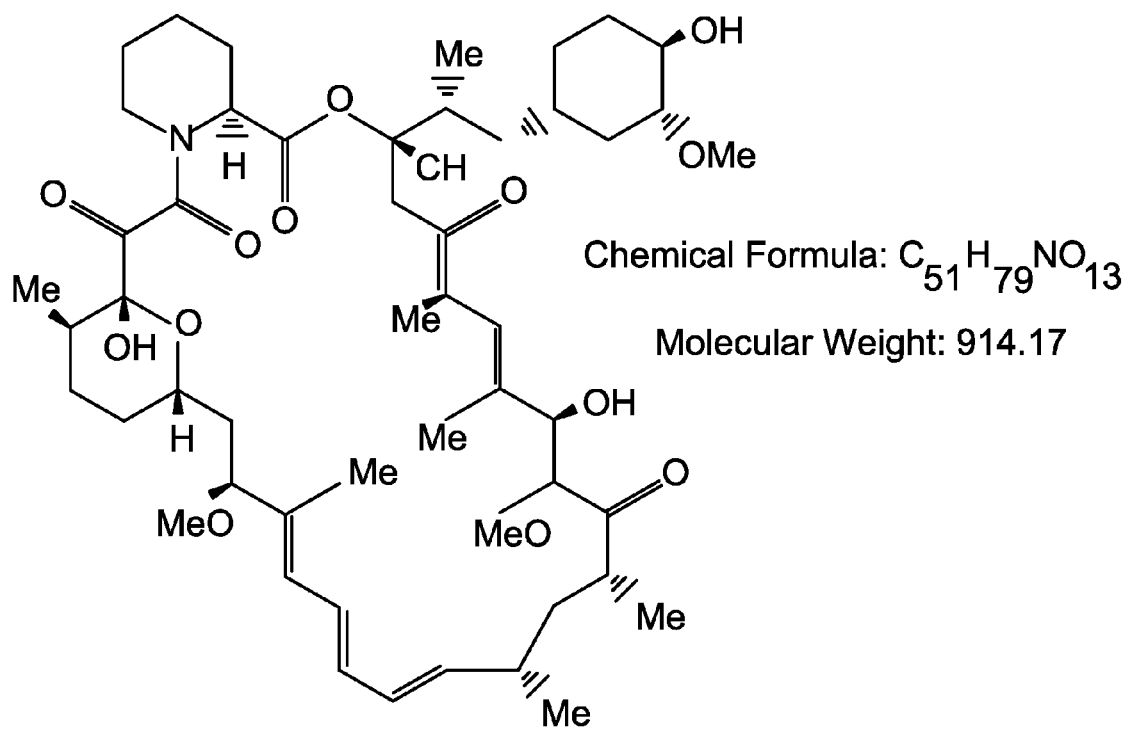
Figure 19:
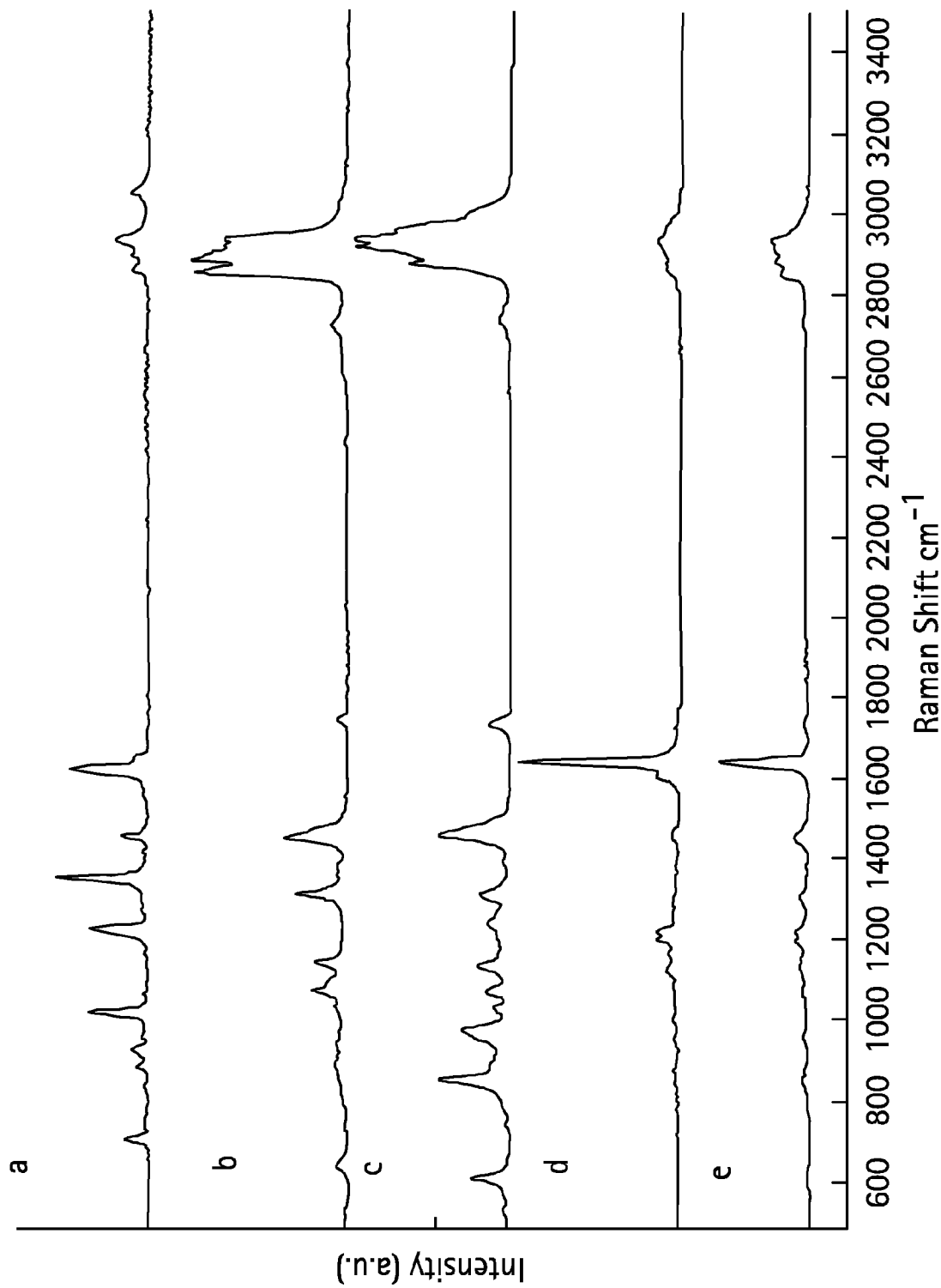
FIG. 19 is a comparison of spectra obtained from each individual component as well as a representative spectrum obtained from a drug-polymer coating sprayed onto a stent

The issue of identifying the unique spectral signatures for quantitative analysis was addressed by analyzing each neat component by Raman spectroscopy. A spectrum of parylene-C, the polymer deposited onto the stent before drug-polymer coating, was also collected to identify its spectral fingerprint. The chemical structures for each component are presented in FIGS. 18a-d. FIG. 18a is parylene-C. FIG. 18b is PEVA. FIG. 18c is PBMA and FIG. 18d is sirolimus. FIG. 8 is a comparison of spectra obtained from each individual component—parylene-C, PEVA, PBAA, and sirolimus in spectra (a-d) respectively as well as a representative spectrum (spectrum (e) of FIG. 19) obtained from a drug-polymer coating sprayed onto a stent. Several key observations can be made from the individual component and drug-polymer coating spectra. Parylene-C has several unique bands, most notably at 3100 cm$^{-1}$ corresponding to the aromatic C-H stretching and the band between 1265-1365 cm$^{-1}$ assigned to CH in-plane deformation (spectrum (a) of FIG. 8). Sirolimus exhibits a unique band in the region between 1600 to 1700 cm$^{-1}$ that is spectrally resolved from the polymer components (spectrum (d) in FIG. 19). This is assigned to the triene band moiety of the molecule based on typical shifts observed for conjugated dienes and CH=CH stretches. Although differences for each component are evident, the integrated sum of the C—H stretching region between 2800-3100 cm$^{-1}$ is useful to calculate a spectral image of the combined coating components. Another region is the broad band between 1400-1500 cm$^{-1}$. This is tentatively assigned to several vibrational modes, including CH$_2$ scissoring and CH$_2$ wagging modes of the polymers and sirolimus (strong band for polymers, weak for sirolimus). The carbonyl stretch is observed for PEVA, PBMA, and sirolimus in the region 1700-1740 cm$^{-1}$. There are spectrally resolved weak to medium intensity bands at 600 and 630 cm$^{-1}$ for PBMA and PEVA respectively (spectra c and b of FIG. 8. These bands are tentatively assigned to C=C—H bending modes. PBMA also has a unique band at 850 cm$^{-1}$. The Raman bands and positions were confirmed by collecting spectra at 785 nm excitation (data not shown). Table 2 summarizes the Raman bands investigated in this work for quantization purposes.

TABLE 2

Band Assignments

| Band Location cm$^{-1}$ | Component | Intensity | Assignment |
|---|---|---|---|
| 600 | PBMA | w-m | C=C—H bending |
| 630 | PEVA | w-m | C=C—H bending |
| 850 | PBMA | m-s | Not assigned |
| 1338 | Parylene-C | s | CH in-plane deformation |
| 1445 | PBMA, PEVA, sirolimus | s | CH$_2$ wag, CH2 scissor |
| 1634 | Sirolimus | vs | CH=CH stretch |

The best spectral feature to identify and quantify sirolimus in the coating was the triene band at ≈1634 cm$^{-1}$ because it is baseline resolved from other spectral features observed in the active layer and it is an intense band due to the large polarizability of the delocalized π electrons. The ratio of the integrated area of the triene band to the integrated area of the 1445 cm$^{-1}$ band that represents both polymer components and sirolimus is calculated. This approach improves the calibration by accomplishing several points: the ratio is an expression of drug content as a fraction related to total drug-polymer content, the ratio calculation reduces the effects of laser intensity variations, and signal intensity variations as a function of depth through the coating are minimized. Both the 1634 and 1445 cm$^{-1}$ bands are medium to strong in scattering intensity and are therefore ideal candidates for quantization of API in relation to total coating content on drug-eluting stents.

To address the quantization of the individual polymers, several options were tried as outlined in Table 2. The spectrally resolved bands at 600 and 630 cm$^{-1}$ unique to PBMA and PEVA were relatively weak in intensity making it difficult to detect at lower concentration levels (less than 28 wt %). For PEVA, most other bands were not spectrally resolved from other active coating components. As an alternative, it was discovered that monitoring the center of mass of the 1445 cm$^{-1}$ band was an indicator of PEVA content. Empirically, an ≈8 cm$^{-1}$ shift in the center of mass between PBMA and PEVA in the pure component spectra was observed. The integrated ratio of the area of the medium-strong band unique to PBMA at 850 cm$^{-1}$ to the sirolimus content (1634 cm$^{-1}$) was chosen to develop the quantitative PBMA model.

Drug Content. Common analytical methods for drug content evaluation include chromatographic determination such as HPLC methods. The laboratory assay to quantify the drug content is used as the reference of the true drug content present in the active coating layer. The drug content was measured both as a composite assay (average of five stents) and an individual stent assay for each formulation. The composite assay serves to verify that the spraying process was successful for each formulation as well as a comparison of stents pre- and post-sterilization. The amount of API ranged from 5 to 50 wt % of the total mass of the stent coating, corresponding to drug contents of 50 to 550 µg. These levels are within the linearity and limit of quantization for the method. Table 3 lists the composite drug content values obtained from each formulation. With the exception of the formulation Group H (50 wt % drug loading), the drug content from stents pre- and post-sterile showed no statistical difference. The difference for Group H is attributed to a small amount of degradation that occurred between the time of manufacture and testing.

TABLE 3

HPLC Assay Values of Drug Content for each Formulation Group

| Sterile samples | Mean sirolimus content (μg) | Mean mass of stents (μg) | Wt % | Non-sterile samples | Mean sirolimus content (μg) | Mean mass of stents (μg) | Wt % |
|---|---|---|---|---|---|---|---|
| A | 51 | 998.4 | 5.1 | A | 50 | 998.4 | 5.0 |
| B | 45 | 975.5 | 4.6 | B | 46 | 976.9 | 4.7 |
| C | 51 | 1014.3 | 5.0 | C | 52 | 1025.1 | 5.1 |
| D | 296 | 993.8 | 29.8 | D | 290 | 984.8 | 29.4 |
| E | 291 | 1011.1 | 28.8 | E | 289 | 1009.7 | 28.6 |
| F | 287 | 1005.8 | 28.5 | F | 292 | 1018.5 | 28.7 |
| G | 460 | 990.9 | 46.4 | G | 468 | 991.1 | 47.2 |
| H | 485 | 1006.2 | 48.2 | H | 441 | 985.9 | 44.7 |
| I | 475 | 997.4 | 47.6 | I | 473 | 1007.7 | 46.9 |
| J | 290 | 1019.4 | 28.4 | J | 286 | 1006.6 | 28.4 |
| K | 282 | 998.8 | 28.2 | K | 290 | 1008.4 | 28.8 |
| L | 392 | 1006.9 | 38.9 | L | 388 | 1014.7 | 38.2 |
| M | 143 | 992.2 | 14.4 | M | 145 | 996.5 | 14.6 |

The individual stent drug content assay was also measured on individual stents after analysis by confocal Raman microscopy. The drug content values for these individual stents were used for the calibration curves as shown in Table 4.

TABLE 4

Comparison HPLC Assay Between Composite Stent and Individual Stent Assay.

| Group | composite sterile wt % sirolimus | Individual sterile stent wt % sirolimus | Difference | Composite nonsterile wt % sirolimus | Individual nonsterile wt % sirolimus | Difference |
|---|---|---|---|---|---|---|
| A | 5.1 | 5.0 | −0.1 | 5.0 | 5.0 | 0.0 |
| B | 4.6 | 4.7 | 0.1 | 4.7 | 4.7 | −0.1 |
| C | 5.0 | 4.9 | −0.1 | 5.1 | 5.0 | −0.1 |
| D | 29.8 | 29.5 | −0.3 | 29.4 | 28.7 | −0.7 |
| E | 28.8 | 28.2 | −0.6 | 28.6 | 27.9 | −0.8 |
| F | 28.5 | 27.9 | −0.6 | 28.7 | 27.9 | −0.8 |
| G | 46.4 | 45.5 | −1.0 | 47.2 | 41.5 | −5.8 |
| H | 48.2 | 47.2 | −1.0 | 44.7 | 38.2 | −6.5 |
| I | 47.6 | 46.0 | −1.6 | 46.9 | 34.4 | −12.5 |
| J | 28.4 | 28.2 | −0.3 | 28.4 | 28.2 | −0.2 |
| K | 28.2 | 27.3 | −1.0 | 28.8 | 27.2 | −1.6 |
| L | 38.9 | 37.4 | −1.5 | 38.2 | 35.4 | −2.8 |
| M | 14.4 | 14.2 | −0.2 | 14.6 | 14.4 | −0.2 |

For the sterile set of samples, the drug content from the averaged stents agreed with the individual stent analyzed post-Raman analysis indicating the method did not degrade the drug. The small deviations observed are within the error of the analytical assay method as well as the uncertainty in the mass of components on the individual stents. For the non-sterile samples, a difference was observed in three formulations containing large amounts of drug (greater than 40 wt %) between the averaged and individual stents. However, several months had elapsed between the time that the averaged stents were assayed compared to the individual stents. Because these stents were not sterile and stored under proper storage conditions, it is plausible that some drug degradation occurred, especially at high drug content loadings in the polymer coating. The comparisons of average versus the individual stent assays for the remaining samples demonstrate that the Raman method is nondestructive to drug content.

Figure 20A:
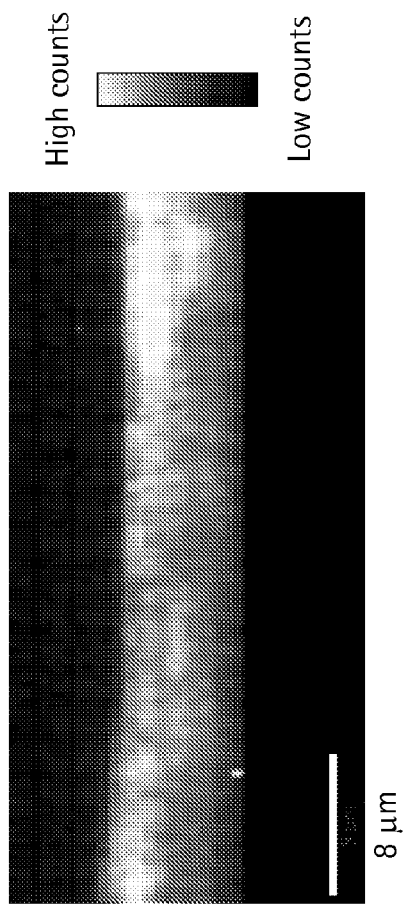
FIGS. 20*a-d* depict examples of a typical Confocal Raman Microscopy (CRM) response.
Figure 20B:
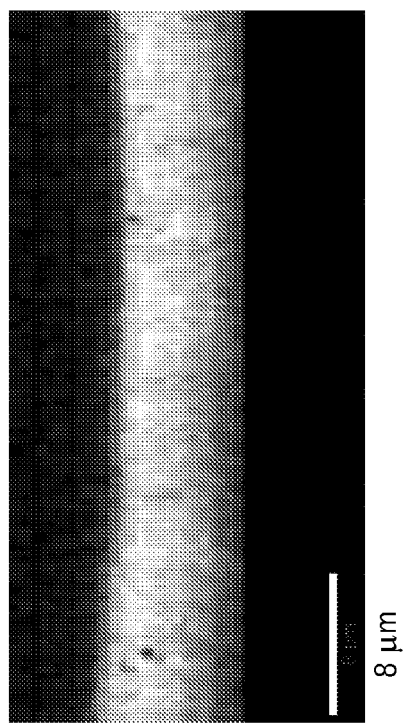
Figure 20C:
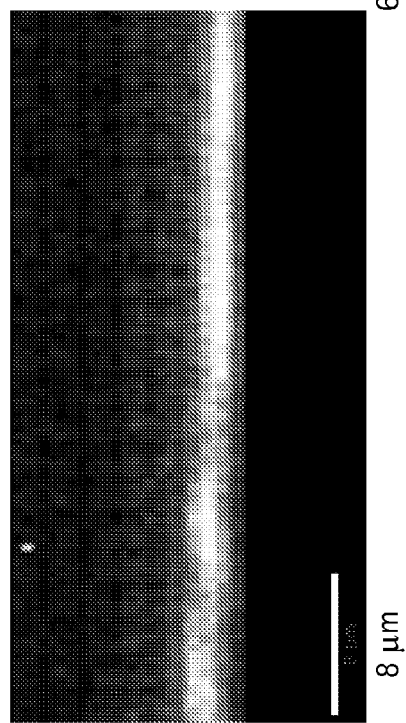
Figure 20D:
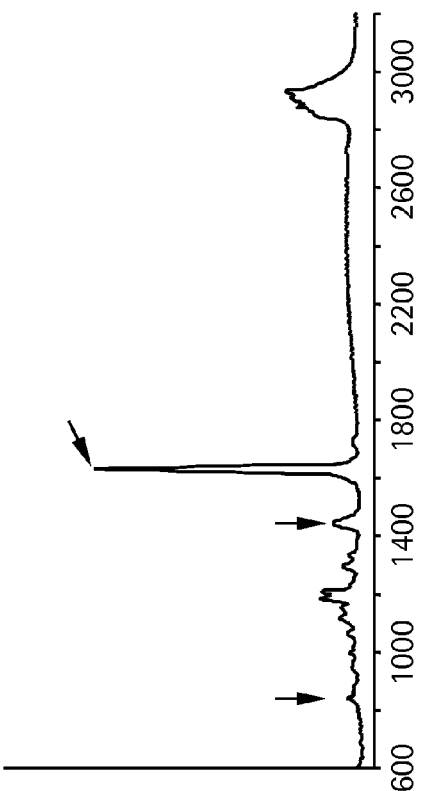

Confocal Raman Microscopy. Examples of a typical CRM response is shown in FIGS. 20a-d. The cross-sectional images of the coating (FIGS. 20a-c) illustrate the transition from air (dark color, low counts, top portion of images) to metal (dark color, low counts, bottom portion of images). Each pixel in the image contains an entire Raman spectrum. To display the 4800 pixel spectral array as an image, the integral of the spectral region 2800-3100 $cm^{-1}$ (methylene stretches) was calculated and displayed in FIG. 20a. The methylene stretching region represents all coating components present in the system, including parylene-C. By displaying this band of the spectral depth image, all coating components present on the stent are revealed. Additional images can be generated based on other characteristics of the spectra, as shown in FIGS. 20b-c. The active ingredient sirolimus is visualized by integrating the triene band at 1634 $cm^{-1}$, FIG. 20b. The signal for the triene band is observed throughout the entire coating, including the coating surface, with intensity variations (indicated by light and dark regions) observed within the 40 by 20 micron spatial region. To properly assess the distribution of drug within a polymer matrix, the spectra within the active drug-polymer coating containing sirolimus must be separated from spectra that are exclusive to the parylene-C layer as well as the regions of air. The image displayed in FIG. 20c is used to distinguish the parylene-C layer from the active drug-polymer layer. A clear distinction is observed in the signal corresponding to the parylene-C and the background signal observed in the drug-polymer coating. FIG. 20d is a typical spectrum that results from averaging the pixels corresponding to the active drug-polymer coating containing sirolimus, PEVA and PBMA. The arrows identify the bands that are used to develop quantitative models for sirolimus, PEVA, and PBMA content.

Figure 21:
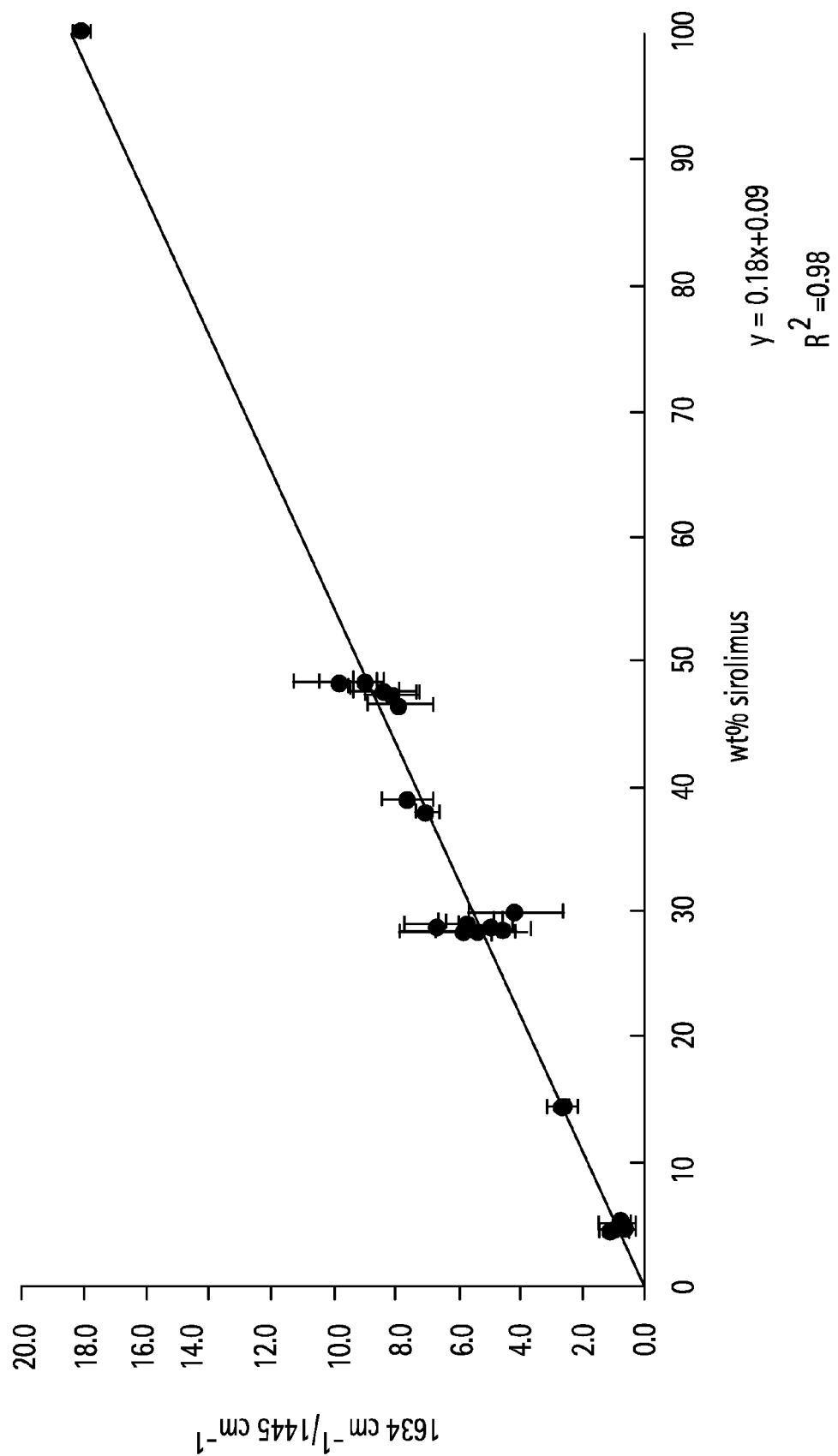
FIG. 21 is a plot of the CRM response for the drug (calculated ratio) versus the weight percent of sirolimus.

Sirolimus Calibration. The calibration for sirolimus content was developed by calculating the integral ratio of two Raman bands present in the spectra (FIG. 20d). For data processing consistency, spectra were exported to GRAMS software and the individual bands fit to a Voigt function. Both the integrated area and the band positions were recorded. A total of 29 stents and 8 planar substrates from 16 different formulations were analyzed by CRM. The ratio of ≈1634 $cm^{-1}$/1445 $cm^{-1}$ Raman bands for these samples was calculated. The wt % of sirolimus in each formulation was calculated from the HPLC-determined drug content divided by mass of the coating for each sample. In FIG. 21, a plot of the CRM response for the drug (calculated ratio) vs. the wt % of sirolimus is shown. For this set of data, the six locations per sample were averaged before to the linear regression. The error bars represent ±1 standard deviation of the mean. The calculated fit had a regression coefficient of 0.98, indicating that this ratio responds to sirolimus concentration linearly from 0 to 100 wt % drug.

Figure 22A:
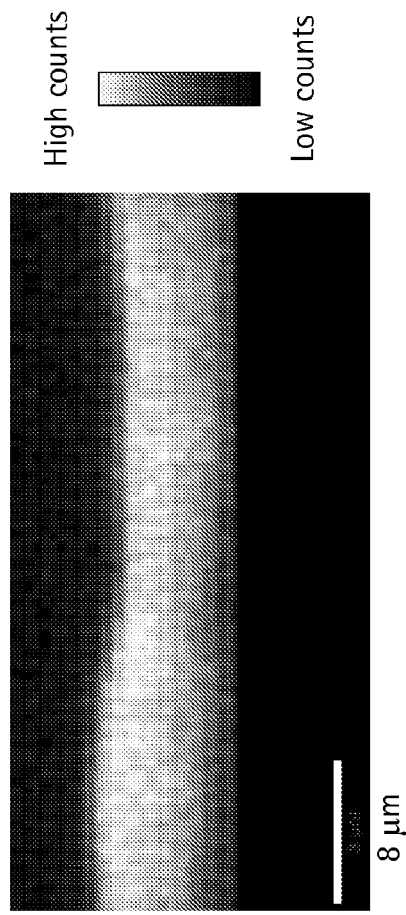
FIGS. 22*a* and 22*b* are examples of the same physical location imaged twice.
Figure 22B:
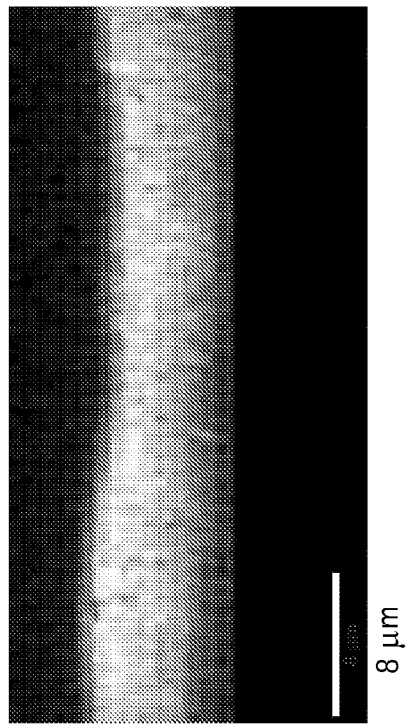
Figure 22C:
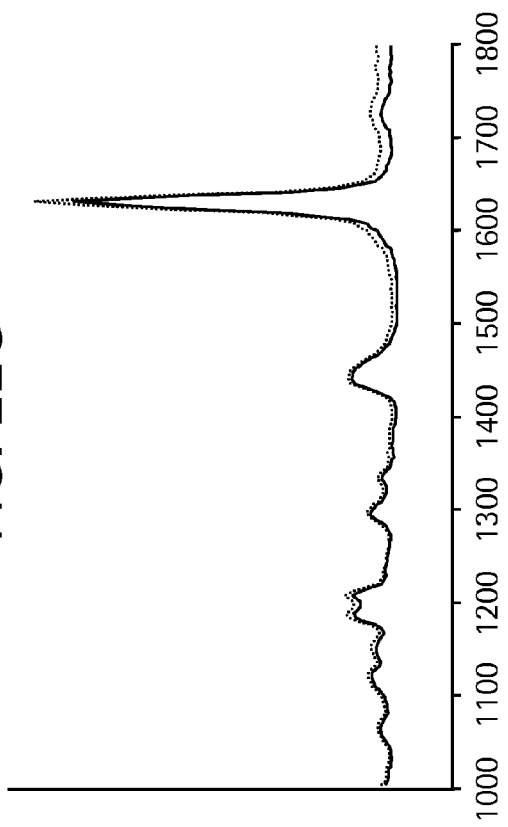
FIG. 22*c* displays the average spectra calculated from the pixels exclusive to the active drug-polymer layer.

To test the reproducibility of CRM as a quantitative technique, spectral depth images of the same coating region were collected as a function of time. Immediately after acquiring the first spectral image, the scan was repeated. Small deviations (less than 1 μm) were sometimes observed in the z dimension indicating small physical movement of the stent relative to the microscope axis each time the microscope stage was reset to the zero position for scanning. FIGS. 22a and 22b are examples of the same physical location imaged twice. In this example, the z movement is undetectable. FIG. 22c displays the average spectra calculated from the pixels exclusive to the active drug-polymer layer. The calculated ratio was 4.4 and 4.2 or a 5% relative variation between measurements. The source of variability is a contribution of the xz position deviations, the user-selected criteria for the selection of pixels corresponding to the active drug-polymer layer, and the instrument noise.

The spatial region sampled by CRM on each stent represents a small fraction of the total coating. A reasonable question arises as to the validity of the method to accurately reflect the true concentration of the sample. Estimating the area sampled in the measurement as 0.0004 $cm^2$, and six locations per sample, it is estimated that 0.12% of the total surface area is profiled by CRM. The assumption made that the six strategically sampled spatial locations, when averaged together, would accurately reflect the bulk drug content described by the HPLC assay. To test this assumption, comparison was made between the calculated ratio from a stent in which the first trial six spatial locations (and two replicated spatial measurements) were profiled and the second trial sampled fourteen spatial locations. The calculated ratios were 4.0±0.7 and 4.3±0.9 respectively. Because collecting additional spatial locations did not reduce the variance and the averages were indistinguishable, it is concluded that six locations are a reasonable approximation of the CRM response to bulk drug content. An additional source of variance is the sample heterogeneity. AFM and DSC confirm the system is heterogeneous in polymer distribution and qualitative Raman images confirm heterogeneity of the drug distribution as well. However, the length scale is different for polymer domains (submicron) compared to drug (several microns laterally).

Figure 23A:
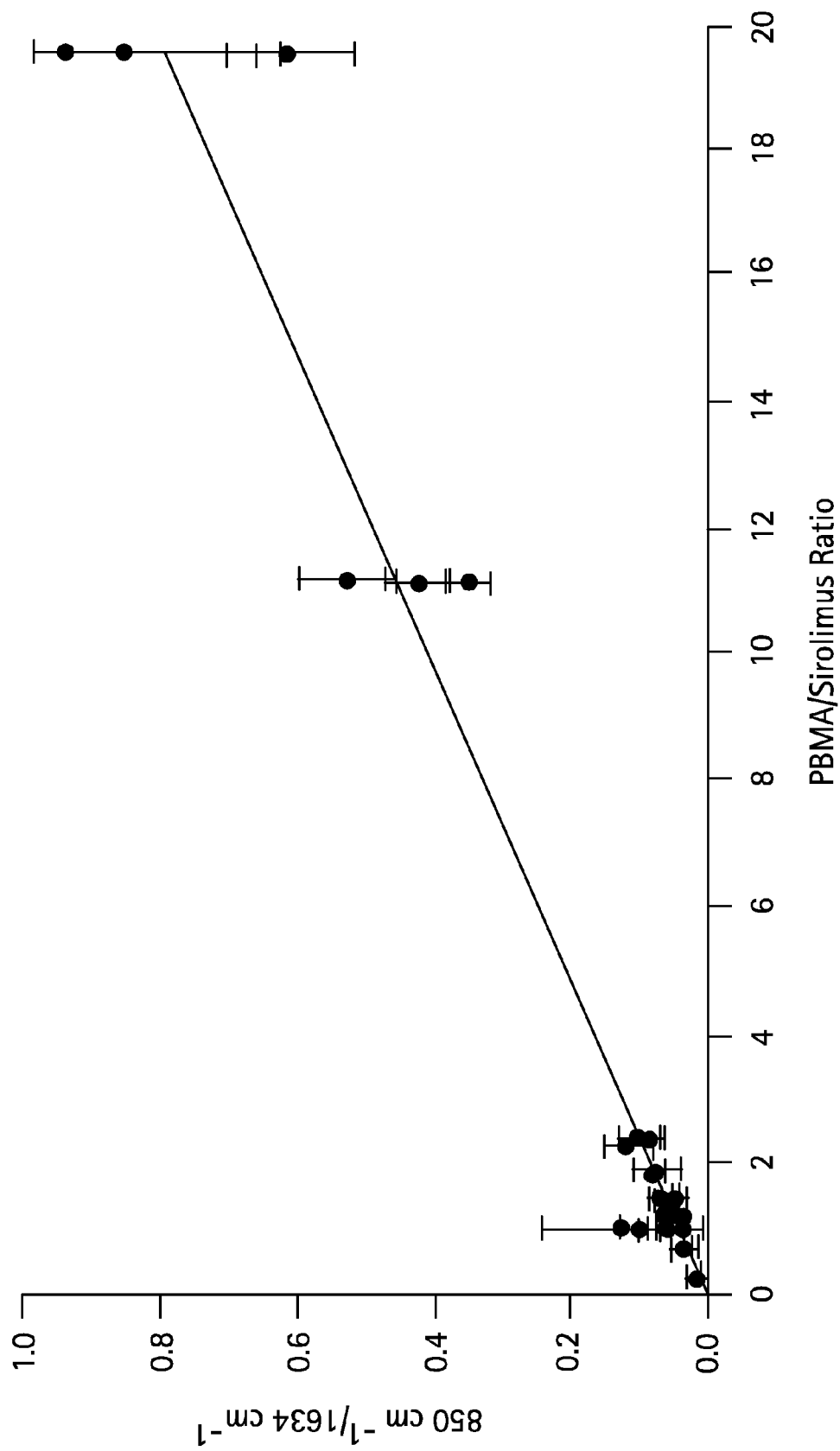
FIG. 23*a* shows the regression curve for PBMA respectively

Polymer calibrations. The calibration curve for PBMA was developed based on the ratio of the 850 $cm^{-1}$ band to the 1634 $cm^{-1}$ band because both Raman bands are exclusive to each respective component and spectrally resolved from other components. Because PEVA does not spectrally interfere with this calculated ratio, the CRM response was plotted versus the concentration of PBMA expressed as a fraction to sirolimus exclusively. The wt % of PBMA on polymer-coated stents was estimated from the solution concentration because a laboratory assay is not available. FIG. 23a shows the regression curve for PBMA. The regression coefficient was 0.96. The error bars represent ±1 standard deviation of the six locations profiled. For comparison, a similar calibration curve was developed from the ratio 850 $cm^{-1}$/1445 $cm^{-1}$ band. This ratio represents the PBMA content to the total content of PEVA, PBMA and sirolimus. The regression coefficient in this case was 0.91 indicating the first calibration is a better fit.

Figure 23B:
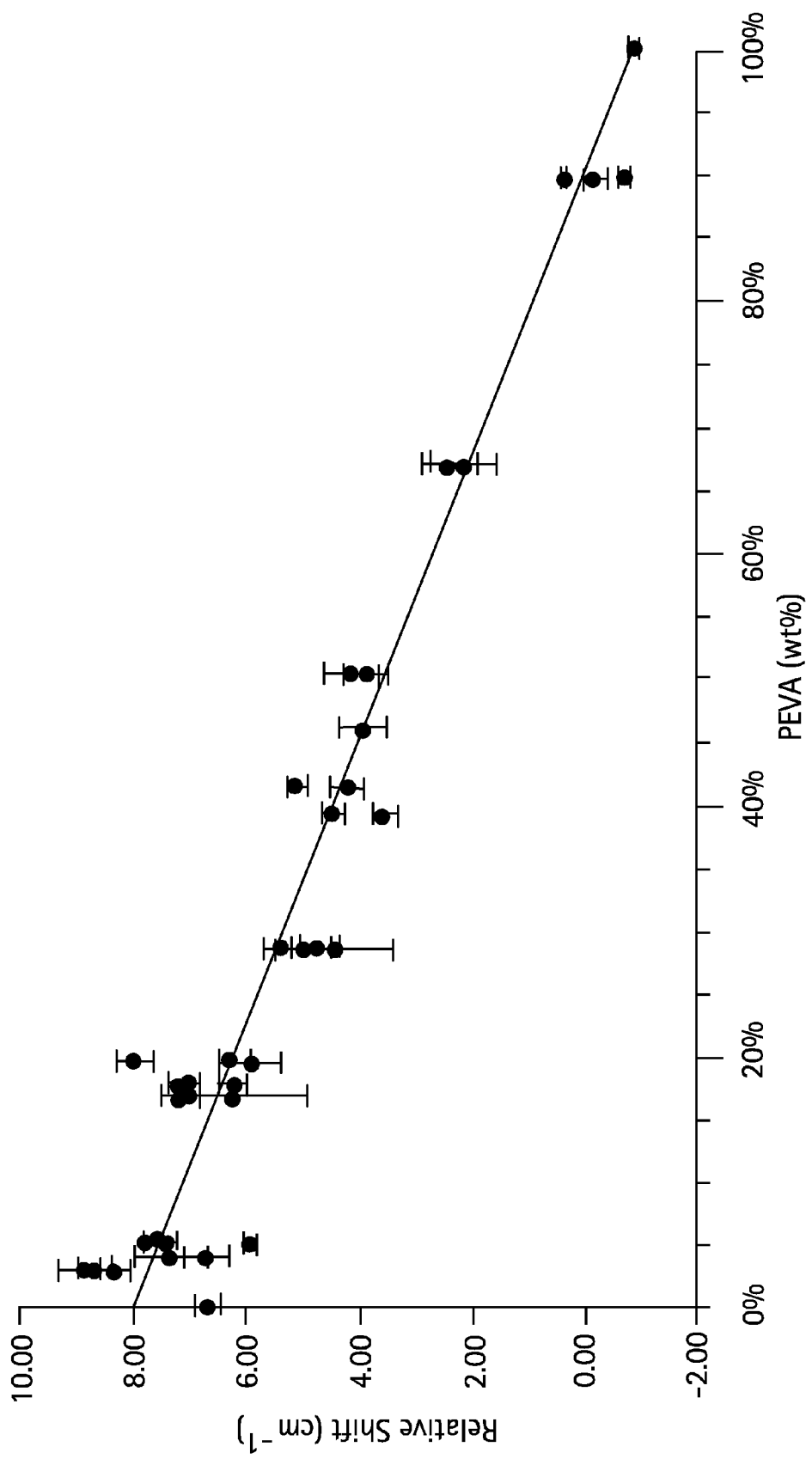
FIG. 23*b* shows the regression curve for PEVA respectively.

With the exception of the 630 $cm^{-1}$ band, PEVA does not exhibit any other bands that do not spectrally interfere from other components. To quantify PEVA, a center of mass dependence of the 1445 $cm^{-1}$ band in response to PEVA concentration was discovered. The relative band shift was calculated by subtracting the 100 wt % band position values for PEVA and PBMA. The relative shift was plotted versus the concentration of PEVA on the stents, which was estimated from the polymer concentration in solution. FIG. 23b shows the regression curve for PEVA. The relative shift in the band with respect to PEVA concentration was linear across the entire range of concentration tested (0 to 100 wt % PEVA). The correlation coefficient was 0.93.

The polymer calibrations were both built on the assumption that the six spatial locations, when averaged together in the calibration, would reflect the bulk polymer content. This is a reasonable assumption because the spatial domains of the polymers are much less than the length scale of the image averaging. Because a laboratory assay is not available that quantifies each polymer separately, the gravimetric analysis from the solution preparation was used as the reference polymer content. Without a laboratory assay for polymer content, the gravimetric analysis reference concentration is an additional source of error for both calibrations and impacts the ability to comment on the accuracy of the models. Qualitatively, each model responds to polymer concentration linearly.

Comparison to ATR-FTIR spectra. An independent spectroscopic technique was used to develop a quantitative response curve for the stent coating components. A limited number of planar samples were measured by ATR-FTIR. Calibration curves were generated for sirolimus as well as the PEVA/PBMA polymer ratio. The total volume sampled is slightly larger compared to confocal Raman because of the depth resolution and spot size difference between the two methods. The sirolimus model was developed by calculating the ratio of the integrated area of the triene band (1634 $cm^{-1}$ unique to sirolimus) to the carbonyl stretch (1710 $cm^{-1}$ present in all components). A linear relationship was observed when plotted against the HPLC assay values. The regression coefficient was 0.98. The polymer ratio calibration was calculated from the 1379 $cm^{-1}$ band (exclusive to PEVA) to the 746 $cm^{-1}$ band (exclusive to PBMA). A linear relationship was observed with a regression coefficient of 0.97.

Independent Samples to Test the Quantitative Models. Using calibration curves generated by the CRM response to changes in concentration, sirolimus, PEVA, and PBMA content were predicted on independent test samples. The average drug content assayed by HPLC from each sample lot was used for comparison because it has been shown in this work to agree well with individual stent analysis. FIG. 14a-d contain representative band sum images corresponding to sirolimus. The images shown correspond to three samples from three unique lots of stents. The distribution of sirolimus was observed throughout the entire area imaged from the air-polymer to polymer-parylene-C interface. The dark intensity regions near the bottom of each image represent the start of the parylene-C layer. Qualitative inspection of Raman images in FIGS. 14a-d shows large domains of greater concentration of drug (greater than 5 μm laterally). A histogram of intensities reveals two distinct distributions, one centered at approximately 300 counts and one centered near 500 counts. The linear regression curve in FIG. 10 was used to predict the sirolimus content for these samples. The mean sirolimus wt % of 10 stents analyzed by HPLC agrees well with the mean sirolimus wt % analyzed by CRM at six spatial locations per one stent. As expected, the variability in the Raman data was larger than the HPLC assay. For the three samples tested, the mean predicted concentration was within 1 wt % of the mean HPLC assay value translating to less than 5% accuracy error in all cases.

TABLE 5

| Sample | Drug Content (wt %) | Std. Deviation n = 10 | Predicted wt % | Std. Deviation n = 6 |
|---|---|---|---|---|
| Sample 1 | 26.8 | 0.1 | 26.6 | 1.6 |
| Sample 2 | 27.0 | 0.2 | 28.5 | 1.4 |
| Sample 3 | 27.6 | 0.1 | 27.4 | 2.2 |

The linear regression curves for PEVA and PBMA were also used to predict concentrations. The predictions of PEVA content for the three samples were within 6 wt % of the solution concentration. The prediction of PBMA content was for the three samples were within 7 wt % of the solution polymer concentrations. Table 6 summarizes the polymer predictions. Conclusions about the accuracy of the polymer predictions cannot be drawn because a laboratory assay for individual polymer content is not available.

TABLE 6

CRM Predicted Polymer Content vs. Gravimetric Analysis

| Sample | PEVA content | Predicted wt % | PBMA content | Predicted wt % |
|---|---|---|---|---|
| Sample 1 | 28 | 24 | 43 | 44 |
| Sample 2 | 28 | 24 | 43 | 38 |
| Sample 3 | 28 | 25 | 43 | 36 |

In the context of this application, confocal microscopy refers to an instrumental technique that allows for depth imaging through a sample. The axis perpendicular to the plane of a sample is referred to as the z dimension and profiles through the transparent or semitransparent sample. Confocal microscopy is achieved with a standard light microscope equipped with an additional aperture (confocal aperture) that decreases the depth of focus. This allows for an xy plane to be preferentially imaged onto the detector, excluding other depths.

As described above, the preferred method of analysis is confocal Raman microscopy (CRM). Confocal Raman microscopy can be combined with or replaced by other spectroscopic methods of analysis to generate the confocal spectral images. For example, confocal fluorescence is achieved by the use of a fluorescence microscope equipped with a confocal aperture. The light microscope would contain an excitation source for fluorescence and band pass filters to select the image range of excitation and emission. Confocal fluorescence microscopy would be useful for API or matrix components that either contain a fluorophore in their molecular composition or are easily tagged with a fluorophore. Depending on the nature of the fluorophores, the output could monitor API distribution, matrix distribution or both. This system could also be used to analyze contact lenses that contain several polymer layers. Again, if an appropriate fluorophore is selected, imaging the distribution of polymer layers within the contact lens is feasible.

A further embodiment would utilize a polarized white light microscope as the analytical instrument 1630. This instrument would be useful to distinguish API from matrix components if the interaction of the polarized white light with the API component is different from the interaction of the polarized white light and the matrix components. In this case, the surface of devices could be examined. An example of this type of application would include detection of a crystalline form of API in a polymer matrix.

Another embodiment of the present invention would utilize XPS imaging as the analytical instrument 1630. This type of analytical instrument would be useful to distinguish elemental information and chemical oxidation states of species within a matrix. An example of this type of application would be the detection of metal ion species (such as silver) within a polymer matrix (such a those found in contact lenses).

An additional embodiment of the present invention utilizes an NIR microscope as the analytical instrument 1630 of the present invention. This type of analysis is useful for characterizing the size of component domains within a matrix. An example of this type of application would be to quantify the average blending of an API within a tablet formation.

Although the preceding specific embodiment has been described with respect to a system that analyzes the coatings on drug-eluting stents, the system of the present invention can be applied to any sample that contains more than one component distributed heterogeneously or homogenously with respect to other components. Specific examples include transdermal medical devices (i.e., nicotine patches, birth control patches, analgesic patches), contact lenses, pharmaceutical tablets, synthetic or natural liposomes, micelles, biological products such as peptides, protein or DNA and emulsions.

With respect to the analysis processing modula, different embodiments can be envisioned depending on whether the instrument analyzes the surface exclusively or profiles through the coating. The types of instruments that can achieve chemical or physical profiling include confocal Raman and fluorescence microscopes, scanning polarized and phase light microscopes, X-ray photoelectron Imaging (XPS Imaging), Near IR Imaging and mass spectrometry imaging such as dynamic static ionization mass spectrometry (dynamic SIMS). These instruments allow for chemical (Raman and fluorescence) and physical (White light microscopy) as well as surface (XPS imaging) versus depth profiling (Raman, fluorescence and dynamic SIMS). Depending on the type of analytical instrument used different frequencies of light are used as the excitation source for analysis.

The data processing module may be modified through the use of various data normalization and filtering preprocessing such as filter by spectrum maximum, filter by spectrum average, criteria of interference such as cosmic rays and fluorescence). Pattern recognition to identify relative spatial locations can be performed by K-means clustering as well as c-means clustering, QT clustering or neural networks. Component identification can be implemented by reference to pure component libraries. Quantitative analysis can also vary depending on the type of model chosen (principal component analysis, partial least squares, multiple linear regression, wavelet analysis and simple linear regression.

An example of quantitative analysis by noise filtration, normalization, K-means clustering, and PCA is shown in FIGS. 24 and 25. This strategy was applied to quantify the API content within a drug-eluting device. For each quantitative method (such as API content), it is necessary to generate a series of standards containing variable amounts of both API and matrix components. The standards are analyzed via the instrumental method. This data is then used to build a calibration model. To validate the calibration model, a second set of samples is required. The number of sample sets can be increased to improve the accuracy and precision of the calibration model. Once a specification is set upon the model, the model can be validated and put into use. The final step involves a series of unknown samples. The model determines and visualizes the distribution of API and matrix components. Table 3 identifies the unique formulations of polyethylene-co-vinyl acetate (PEVA), polybutyl methacrylate (PBMA), and Rapamycin. The formulations were sprayed onto 9 cell by 13 mm stainless steel Bx Velocity stents that contained a parylene C polymer layer. The spraying occurred at a fixed relative humidity. The data was collected on 17 out of 30 formulation groups with a confocal Raman microscope.

TABLE 3

| Formulation Groups | rapamycin | PEVA | PBMA |
|---|---|---|---|
| A | 33% | 33% | 33% |
| B | 25% | 25% | 50% |
| C | 25% | 50% | 25% |
| D | 20% | 40% | 40% |
| E | 50% | 25% | 25% |
| F | 40% | 20% | 40% |
| G | 40% | 40% | 20% |
| H | 0% | 5% | 95% |
| I | 0% | 25% | 75% |
| J | 0% | 50% | 50% |
| K | 0% | 75% | 25% |
| L | 0% | 95% | 5% |
| M | 5% | 5% | 90% |
| N | 5% | 24% | 71% |
| O | 5% | 48% | 48% |
| P | 5% | 71% | 24% |
| Q | 5% | 90% | 5% |
| R | 9% | 5% | 86% |
| S | 9% | 23% | 68% |
| T | 9% | 45% | 45% |
| U | 9% | 68% | 23% |
| V | 9% | 86% | 5% |
| W | 20% | 4% | 76% |
| X | 20% | 20% | 60% |
| Y | 20% | 40% | 40% |
| Z | 20% | 60% | 20% |
| AA | 20% | 76% | 4% |
| BB | 33% | 3% | 63% |
| CC | 33% | 17% | 50% |
| DD | 33% | 33% | 33% |
| EE | 33% | 50% | 17% |
| FF | 33% | 63% | 3% |

The data analysis consisted of first normalizing and filtering the spectra contained within xz spectral image profiles. Each file contained 4800 spectra with 1024 points per spectra. The data was filtered to exclude the Rayleigh line (first 150 points). The normalization was performed according to the equation (2) where $z_i$—normalized value; $x_i$—source value.

$$z_i = \frac{x_i - \min_i(x_i)}{\max_i(x_i) - \min_i(x_i)} \quad (2)$$

The global (for the whole spectral image) minimum and maximum values are used for the normalization. Otherwise, a normalized spectrum for air or metal looks like a random value from 0 to 1. Next, the cosmic rays were removed from the data by setting a threshold value. Values above the threshold were considered cosmic rays and the value at this point was changed to the value of the intensity of the average of the neighbor's intensities. Fluorescence was also filtered from the data by setting a width threshold value for bands observed in the spectra. If the width was greater than 630 cm$^{-1}$ it was considered to contain fluorescence and excluded. Finally, to identify the most informative factors, 5 regions within the spectra were identified as the most informative. This preprocessed data set was then subjected to K-mean cluster analysis. The clusters that resulted were manually defined as to which cluster belonged to the API/polymer layer. An example cluster image is shown in FIG. 24a.

The spectra that were selected by cluster analysis were then used in a principle component model to build a model for API concentration. FIG. 25 contains a plot of predicted API weight % versus experimental API wt % (determined via an analytical drug content method). The correlation is 0.625386. The model is not acceptable for practical use, but demonstrates the strategy involved to develop a correlation between experimental and predicted data. FIG. 24b is a quantitative visual representation of a stent based on this model.

The visualization of the data can utilize the preprocessing step to display quantitative images representing the spatial distribution of components as a map of the intensity of the relevant spectroscopic signal. Other examples of visualization would include particle size analysis, impurity analysis and quantization of chemical domains.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A system for a non-destructive analysis of a spatial distribution and identification of one or more components of an object without addition of an image enhancement agent comprising:
   a sample and analysis tracking module for collecting and storing information about the object;
   an analysis processing module to collect data regarding the distribution of components of the object and information regarding collection of the data; and
   a data processing module for analytically processing the data to determine the spatial distribution and identification of the one or more components of the object.

2. The system of claim 1 wherein the sample and analysis tracking module collects and stores a description of the object, fabrication date of the object, and the analysis date.

3. The system of claim 1 wherein the analysis processing module comprises an analytical instrument for collecting information about the object.

4. The system of claim 3 wherein the analytical instrument comprises a confocal Raman microscope.

5. The system of claim 3 wherein the analysis processing module further comprises a positioning device for controlling the position of the object relative to the analytical instrument.

6. The system of claim 5 wherein the analysis processing module further comprises a bar code scanner for reading an identifying bar code on the object.

7. The system of claim 6 wherein the analysis processing module further comprises a programmable logic controller for controlling the functions of the analytical instrument, positioning device and bar code scanner.

8. The system of claim 1 wherein the output of the data processing module includes information about the composition of components and the spatial distribution of components of the object including identification of manufacturing and formulation defects of the object.

9. The system of claim 8 wherein the output is displayed as a visual representation.

10. The system of claim 8 wherein the output is displayed as a numeric representation.

11. The system of claim 1 further comprising a central database that receives and stores data from the analysis processing module and the data processing module.

12. The system of claim 3 wherein the analytical instrument is selected from the group consisting of: a confocal Raman microscope, a confocal fluorescence microscope, a scanning polarized and phased light microscope, an x-ray photoelectron imaging system, a near IR Imaging system and a dynamic static ionization mass spectrometer (dynamic SIMS).

13. The system of claim 1 wherein the data processing module comprises a filter to filter the data received from the analysis processing module to remove noise.

14. The system of claim 13 wherein the filter removes noise from the data resulting from cosmic rays.

15. The system of claim 13 wherein the filter comprises a band-pass filter used to exclude the laser line at the detector of a confocal Raman microscope.

16. The system of claim 1 wherein the data processing module comprises a clustering algorithm.

17. The system of claim 16 wherein the clustering algorithm is the K-means clustering algorithm.

18. The system of claim 1 further comprising a set of training sets and validation sets for each type of object to be analyzed.

19. A method for a non-destructive analysis of a spatial distribution and identification of one or more components of a an object without the use of image enhancement agents comprising the steps of:
collecting and storing information about the object;
collecting data regarding the distribution of components of the object and information on the collection of the data; and,
analytically processing the data in a data processing module to determine the spatial distribution and identification of the one or more components of the object.

20. The method of claim 19 wherein the step of collecting and storing information about the object includes collecting and storing a description of the object, the fabrication date of the object, and/or the analysis date of testing.

21. The method of claim 19 wherein confocal Raman microscopy is used to collect data regarding the distribution of components of the object.

22. The method of claim 19 wherein the step of collecting data uses an analytical instrument selected from the group consisting of: a confocal Raman microscope, a confocal fluorescence microscope, a scanning polarized and phased light microscope, and x-ray photoelectron imaging system, a near IR imaging system and a dynamic static ionization mass spectrometer (dynamic SIMS).

23. The method of claim 19 wherein the output of the step of analytically processing the data includes outputting information about the composition of components of the object, the distribution of components within the object and identification of manufacturing and formulation defects of the object.

24. The method of claim 23 wherein the output is displayed as a visual representation.

25. The method of claim 23 wherein the output is displayed as a numeric representation.

26. The method of claim 19 wherein the step of analytically processing the data further includes the steps of:
filtering the data to remove noise;
standardizing the data;
performing a clustering algorithm on the data;
comparing the data to one or more training sets and validations set for a specific type of test sample;
building a model of the quantitative spatial distribution of the components in the object;
calibrating the model using PCA and linear regression techniques; and,
generating a visualization of the quantitative spatial distribution of components of the object for output to the user.

27. The method of claim 19 further comprising the step of storing data about the object and the spatial distribution of component in the object in a central database.

28. A system for a non-destructive analysis of a spatial distribution and identification of one or more components of a coating applied to a medical device without use of an image enhancement agent comprising:
a sample and analysis tracking module for collecting and storing a description of the medical device;
an analysis processing module comprising an analytical instrument, positioning device and a programmable controller used to collect data regarding the distribution of components of the coating applied to the medical device;
a data processing module for analytically processing the data to determine the spatial distribution and identification of the one or more components of the medical device; and,
a central database in communication with the sample analysis tracking module, and the data processing module for storing information and data regarding the medical device.

29. The system of claim 28 wherein the analytical instrument comprises a confocal Raman microscope.

30. The system of claim 28 wherein the analytical instrument is selected from the group consisting of: a confocal Raman microscope, a confocal fluorescence microscope, a scanning polarized and phased light microscope, an x-ray photoelectron imaging system, a near IR imaging system and a dynamic static ionization mass spectrometer.

31. The system of claim 28 wherein the data processing module comprises a filter to filter the data received from the analysis processing module to remove noise.

32. The system of claim 31 wherein the filter removes noise from the data resulting from cosmic rays.

33. The system of claim 29 wherein the filter comprises a band-pass filter used to exclude the laser line at the detector of the confocal Raman microscope.

34. The system of claim 28 wherein the data processing module comprises a clustering algorithm.

35. The system of claim 34 wherein the clustering algorithm is the K-means clustering algorithm.

36. A method for a non-destructive analysis of a spatial distribution and identification of one or more components of a coating applied to a medical device without use of image enhancement agents comprising the steps of:
collecting and storing information about the medical device;
collecting data regarding the distribution of components in the coating applied to the medical device using an analytical instrument and positioning device; and,
analytically processing the data in a data processing module to determine the spatial distribution and identification of the one or more components in the coating applied to the medical device.

37. The method of claim 36 wherein confocal Raman microscopy is used to collect data regarding the distribution of components of the coating on the medical device.

38. The method of claim 36 wherein the step of analytically processing the data further includes the steps of:

filtering the data to remove noise;

standardizing the data;

performing a clustering algorithm on the data;

comparing the data to one or more training sets and validations set for a specific type of test sample;

building a model of the quantitative spatial distribution of the components in the coating applied to the medical device;

calibrating the model using PCA and linear regression techniques; and, generating a visualization of the quantitative spatial distribution of components of the coating for output to the user.

39. The method of claim 36 wherein the medical device is a drug-eluting stent having an active pharmaceutical ingredient (API) in a polymer matrix.

40. The method of claim 39 wherein the output of the step of analytically processing the data includes outputting information about the API content, API distribution, polymer matrix content, polymer matrix distribution, coating thickness and identification of manufacturing and formulation defects of the coating on the stent.

* * * * *